United States Patent
Provost et al.

(10) Patent No.: US 7,547,469 B2
(45) Date of Patent: Jun. 16, 2009

(54) FORMING LOOP MATERIALS

(75) Inventors: George A. Provost, Litchfield, NH (US); James R. Barker, Francestown, NH (US)

(73) Assignee: Velcro Industries B.V., Curacao (NL)

( * ) Notice: Subject to any disclaimer, the term of this patent is extended or adjusted under 35 U.S.C. 154(b) by 16 days.

(21) Appl. No.: 11/102,456

(22) Filed: Apr. 8, 2005

(65) Prior Publication Data

US 2005/0208259 A1    Sep. 22, 2005

Related U.S. Application Data

(63) Continuation-in-part of application No. 10/728,138, filed on Dec. 3, 2003, now Pat. No. 7,156,937.

(60) Provisional application No. 60/430,731, filed on Dec. 3, 2002.

(51) Int. Cl.
*B32B 33/00* (2006.01)
*D04H 1/46* (2006.01)

(52) U.S. Cl. .............................. 428/88; 428/92; 428/95; 428/96; 442/402

(58) Field of Classification Search .................... None
See application file for complete search history.

(56) References Cited

U.S. PATENT DOCUMENTS

| | | | |
|---|---|---|---|
| RE18,001 E * | 3/1931 | Rayner | .................. 28/107 |
| 2,706,324 A | 4/1955 | Cogovan | |
| 3,047,444 A | 7/1962 | Harwood | |
| 3,348,992 A | 10/1967 | Cochran, II | |
| 3,408,417 A | 10/1968 | Sogawa et al. | |
| 3,496,260 A | 2/1970 | Guenther et al. | |
| 3,535,178 A | 10/1970 | Parlin et al. | |
| 3,577,607 A | 5/1971 | Ikoma et al. | |
| 3,674,618 A | 7/1972 | Spann | |
| 3,694,867 A | 10/1972 | Stumpf | |
| 3,704,191 A | 11/1972 | Buresh et al. | |
| 3,705,065 A | 12/1972 | Stumpf | |
| 3,708,361 A | 1/1973 | Stumpf | |
| 3,819,462 A | 6/1974 | Starr et al. | |
| 3,822,162 A | 7/1974 | Stumpf | |
| 3,940,525 A | 2/1976 | Ballard | |
| 3,949,128 A | 4/1976 | Ostermeier | |
| 3,950,587 A | 4/1976 | Colijn et al. | |

(Continued)

FOREIGN PATENT DOCUMENTS

DE    101 39 842 A1    4/2003

(Continued)

OTHER PUBLICATIONS

Dilo Group, "Market Leadership in Nonwovens Technology", Pakistan Textile Journal, date unknown (2 pages).

(Continued)

*Primary Examiner*—Jenna-Leigh Johnson
(74) *Attorney, Agent, or Firm*—Fish & Richardson P.C.

(57) ABSTRACT

Loop materials are provided for touch fastening. Some loop materials include a flexible sheet-form substrate, and hook-engageable fibers secured individually and directly to the substrate, the fibers being disposed in discrete fastening regions of the substrate, leaving fiber-free substrate between adjacent fastening regions. Methods of making and using such loop materials are also provided.

27 Claims, 12 Drawing Sheets

U.S. PATENT DOCUMENTS

| | | | |
|---|---|---|---|
| 4,001,472 A | 1/1977 | Thomas et al. | |
| 4,010,302 A | 3/1977 | Anderson et al. | |
| 4,035,533 A | 7/1977 | Chambley | |
| 4,116,892 A | 9/1978 | Schwarz | |
| 4,131,704 A | 12/1978 | Erickson et al. | |
| 4,154,885 A | 5/1979 | Tecl et al. | |
| 4,154,889 A | 5/1979 | Platt | |
| 4,192,086 A | 3/1980 | Sichak | |
| 4,223,059 A | 9/1980 | Schwarz | |
| 4,258,094 A | 3/1981 | Benedyk | |
| 4,258,097 A | 3/1981 | Benedyk | |
| 4,295,251 A | 10/1981 | Tatham et al. | |
| 4,315,965 A | 2/1982 | Mason et al. | |
| 4,320,167 A | 3/1982 | Wishman | |
| 4,324,824 A | 4/1982 | Narens et al. | |
| 4,342,802 A | 8/1982 | Pickens, Jr. et al. | |
| 4,363,845 A | 12/1982 | Hartmann | |
| 4,377,889 A | 3/1983 | Tatham et al. | |
| 4,379,189 A | 4/1983 | Platt | |
| 4,389,442 A | 6/1983 | Pickens, Jr. et al. | |
| 4,389,443 A | 6/1983 | Thomas et al. | |
| 4,391,866 A | 7/1983 | Pickens, Jr. et al. | |
| 4,418,104 A | 11/1983 | Kiyomura et al. | |
| 4,439,476 A | 3/1984 | Guild | |
| 4,446,189 A | 5/1984 | Romanek | |
| 4,451,314 A | 5/1984 | Knoke et al. | |
| 4,451,315 A | 5/1984 | Miyazaki | |
| 4,490,425 A | 12/1984 | Knoke et al. | |
| 4,521,472 A | 6/1985 | Gold | |
| 4,536,439 A | 8/1985 | Forsten | |
| 4,600,605 A | 7/1986 | Nakai et al. | |
| 4,600,618 A | 7/1986 | Raychok, Jr. et al. | |
| 4,609,581 A | 9/1986 | Ott | |
| 4,645,699 A | 2/1987 | Neveu | |
| 4,654,246 A | 3/1987 | Provost et al. | |
| 4,750,443 A | 6/1988 | Blaustein et al. | |
| 4,761,318 A | 8/1988 | Ott et al. | |
| 4,770,917 A | 9/1988 | Tochacek et al. | |
| 4,931,343 A | 6/1990 | Becker et al. | |
| 4,973,326 A | 11/1990 | Wood et al. | |
| 5,032,122 A | 7/1991 | Noel et al. | |
| 5,066,289 A | 11/1991 | Polski | |
| 5,080,951 A | 1/1992 | Guthrie | 428/85 |
| 5,144,730 A | 9/1992 | Dilo | |
| 5,216,790 A | 6/1993 | Eschenbach | |
| 5,254,194 A | 10/1993 | Ott et al. | |
| 5,256,231 A | 10/1993 | Gorman et al. | |
| 5,304,162 A | 4/1994 | Kuen | |
| 5,307,616 A | 5/1994 | Goineau et al. | |
| 5,320,890 A * | 6/1994 | Anton et al. | 428/90 |
| 5,326,612 A | 7/1994 | Goulait | |
| 5,379,501 A | 1/1995 | Goineau | |
| 5,380,313 A | 1/1995 | Gonlait et al. | |
| 5,380,580 A | 1/1995 | Rogers et al. | |
| 5,382,461 A | 1/1995 | Wu | |
| 5,383,873 A | 1/1995 | Hoey et al. | |
| 5,386,595 A | 2/1995 | Kuen et al. | |
| 5,391,424 A | 2/1995 | Kolzer | |
| 5,403,302 A | 4/1995 | Roessler et al. | |
| 5,407,439 A | 4/1995 | Goulait | |
| 5,407,722 A | 4/1995 | Peake, III et al. | |
| 5,417,902 A | 5/1995 | Bennie et al. | |
| 5,423,789 A | 6/1995 | Kuen | |
| 5,447,590 A | 9/1995 | Gilpatrick | |
| 5,449,530 A | 9/1995 | Peake, III et al. | |
| 5,459,991 A | 10/1995 | Nabeshima | |
| 5,470,417 A | 11/1995 | Goulait | |
| 5,476,702 A | 12/1995 | Datta et al. | |
| 5,500,268 A | 3/1996 | Billarant | |
| 5,518,795 A | 5/1996 | Kennedy et al. | |
| 5,531,732 A | 7/1996 | Wood | |
| 5,542,942 A | 8/1996 | Kline et al. | |
| 5,547,531 A | 8/1996 | Allen et al. | |
| 5,554,239 A | 9/1996 | Datta et al. | |
| 5,569,233 A | 10/1996 | Goulait | |
| 5,571,097 A | 11/1996 | Seth | |
| 5,595,567 A | 1/1997 | King et al. | |
| 5,599,601 A | 2/1997 | Polski et al. | |
| 5,603,708 A | 2/1997 | Seth | |
| 5,605,729 A | 2/1997 | Mody et al. | |
| 5,611,789 A | 3/1997 | Seth | |
| 5,611,791 A | 3/1997 | Gorman et al. | |
| 5,614,232 A | 3/1997 | Torigoe et al. | |
| 5,614,281 A | 3/1997 | Jackson et al. | |
| 5,615,460 A | 4/1997 | Weirich et al. | |
| 5,616,155 A | 4/1997 | Kronzer | |
| 5,616,394 A | 4/1997 | Gorman et al. | |
| 5,620,779 A | 4/1997 | Levy et al. | |
| 5,622,578 A | 4/1997 | Thomas | |
| 5,624,427 A | 4/1997 | Bergman et al. | |
| 5,630,896 A | 5/1997 | Corbin et al. | |
| 5,643,397 A | 7/1997 | Gorman et al. | |
| 5,647,864 A | 7/1997 | Allen et al. | |
| 5,654,070 A | 8/1997 | Billarant | |
| 5,660,911 A | 8/1997 | Tesch | |
| 5,669,593 A | 9/1997 | Kirchner | |
| 5,669,900 A | 9/1997 | Bullwinkel et al. | |
| 5,669,901 A | 9/1997 | LaFourtune et al. | |
| 5,685,756 A | 11/1997 | Noda | |
| 5,686,163 A | 11/1997 | Tsubata et al. | |
| 5,692,949 A | 12/1997 | Sheffield et al. | |
| 5,707,707 A | 1/1998 | Burnes et al. | |
| 5,707,906 A | 1/1998 | Eschenbach | |
| 5,722,968 A | 3/1998 | Datta et al. | |
| 5,735,453 A | 4/1998 | Gick et al. | |
| 5,736,214 A | 4/1998 | Billarant | |
| 5,759,926 A | 6/1998 | Pike et al. | |
| 5,763,041 A | 6/1998 | Leak et al. | |
| 5,766,723 A | 6/1998 | Oborny et al. | |
| 5,773,120 A | 6/1998 | Deka et al. | |
| 5,786,060 A | 7/1998 | Takahashi et al. | |
| 5,814,390 A | 9/1998 | Stokes et al. | |
| 5,830,298 A | 11/1998 | Jackson | |
| 5,843,057 A | 12/1998 | McCormack | |
| 5,858,515 A | 1/1999 | Stokes et al. | |
| 5,866,222 A | 2/1999 | Seth et al. | |
| 5,888,607 A | 3/1999 | Seth et al. | |
| 5,891,547 A | 4/1999 | Lawless | |
| 5,904,793 A | 5/1999 | Gorman et al. | |
| 5,931,823 A | 8/1999 | Stokes et al. | |
| 5,945,215 A | 8/1999 | Bersted et al. | |
| 5,962,102 A | 10/1999 | Sheffield et al. | |
| 5,962,112 A | 10/1999 | Haynes et al. | |
| 5,964,742 A | 10/1999 | McCormack et al. | |
| 5,997,981 A | 12/1999 | McCormack et al. | |
| 6,051,094 A | 4/2000 | Melbye et al. | |
| 6,086,984 A | 7/2000 | DiMaggio, Jr. et al. | |
| 6,093,665 A | 7/2000 | Sayovitz et al. | |
| 6,129,879 A | 10/2000 | Bersted et al. | |
| 6,129,964 A | 10/2000 | Seth | |
| 6,158,097 A | 12/2000 | Dilo | |
| 6,161,269 A | 12/2000 | Dilo et al. | |
| 6,162,522 A | 12/2000 | Deka et al. | |
| 6,192,556 B1 | 2/2001 | Kikko et al. | |
| 6,195,850 B1 | 3/2001 | Melbye et al. | |
| 6,265,053 B1 | 7/2001 | Kronzer et al. | |
| 6,329,016 B1 | 12/2001 | Shepard et al. | |
| 6,342,285 B1 | 1/2002 | Shepard et al. | |
| 6,355,759 B1 | 3/2002 | Sherman et al. | |
| 6,368,444 B1 | 4/2002 | Jameson et al. | |
| 6,410,138 B2 | 6/2002 | Mleziva et al. | |
| 6,454,989 B1 | 9/2002 | Neely et al. | |
| 6,489,004 B1 | 12/2002 | Martin et al. | |
| 6,537,935 B1 | 3/2003 | Seth et al. | |

| | | | | | |
|---|---|---|---|---|---|
| 6,598,276 B2 | 7/2003 | Shepard et al. | JP | 6-33359 | 2/1994 |
| 6,638,611 B2 | 10/2003 | Seth | JP | 06-123061 | 5/1994 |
| 6,642,160 B1 | 11/2003 | Takahashi | JP | 7-171011 | 7/1995 |
| 6,642,429 B1 | 11/2003 | Carter et al. | JP | 08-27657 | 1/1996 |
| 6,645,611 B2 | 11/2003 | Seth | JP | 09 003755 | 1/1997 |
| 6,660,202 B2 | 12/2003 | Shepard et al. | JP | 09-195154 | 7/1997 |
| 6,686,303 B1 | 2/2004 | Haynes et al. | JP | 09-195155 | 7/1997 |
| 6,703,086 B2 | 3/2004 | Kronzer et al. | JP | 09-241961 | 9/1997 |
| 6,709,996 B2 | 3/2004 | Mleziva et al. | JP | 10-146207 | 6/1998 |
| 6,716,511 B2 | 4/2004 | Bersted et al. | JP | 10-151005 | 6/1998 |
| 6,740,385 B2 | 5/2004 | Gardner et al. | JP | 2971332 | 11/1999 |
| 6,756,327 B2 | 6/2004 | Martin | JP | 2000-314065 | 11/2000 |
| 6,783,834 B2 | 8/2004 | Shepard et al. | JP | 2001-212 | 1/2001 |
| 6,849,142 B1 | 2/2005 | Goulait | JP | 2001-8713 | 1/2001 |
| 6,869,659 B2 | 3/2005 | Shepard et al. | JP | 3134709 | 2/2001 |
| 6,948,221 B2 | 9/2005 | Fuchs | JP | 2001-207369 | 8/2001 |
| 6,955,847 B1 | 10/2005 | Itou et al. | JP | 2001-514346 | 9/2001 |
| 7,117,571 B2 | 10/2006 | Dilo | JP | 2002-10807 | 1/2002 |
| 7,156,937 B2 | 1/2007 | Provost et al. | JP | 2003-265207 | 9/2003 |
| 7,276,642 B2 | 10/2007 | Belau | JP | 2004-194730 | 7/2004 |
| 7,282,251 B2 | 10/2007 | Provost et al. | JP | 3855084 | 12/2006 |
| 2001/0051253 A1 | 12/2001 | Tai et al. | JP | 3877842 | 2/2007 |
| 2003/0077430 A1 | 4/2003 | Grimm et al. | WO | WO 92/01401 | 2/1992 |
| 2003/0119404 A1* | 6/2003 | Belau et al. ............ 442/361 | WO | WO 95/17111 | 6/1995 |
| 2004/0020579 A1 | 2/2004 | Durrance et al. | WO | WO98/33410 | 8/1998 |
| 2004/0072491 A1 | 4/2004 | Gillette et al. | WO | WO99/11452 | 3/1999 |
| 2004/0131820 A1 | 7/2004 | Turner | WO | WO 00/40793 | 7/2000 |
| 2004/0157036 A1 | 8/2004 | Provost et al. | WO | WO 00/42964 | 7/2000 |
| 2004/0163221 A1 | 8/2004 | Shepard et al. | WO | WO01/80680 | 1/2001 |
| 2004/0229008 A1* | 11/2004 | Hoying ............ 428/92 | WO | WO 02/100207 | 12/2002 |
| 2005/0196580 A1 | 9/2005 | Provost et al. | WO | WO03/051251 | 6/2003 |
| 2005/0196581 A1 | 9/2005 | Provost et al. | WO | WO2004/019305 | 3/2004 |
| 2005/0196583 A1 | 9/2005 | Provost et al. | WO | WO 2004/049853 | 6/2004 |
| 2005/0217092 A1 | 10/2005 | Barker et al. | WO | WO2004/049853 | 6/2004 |
| 2005/0281976 A1 | 12/2005 | Curro et al. | WO | WO2004/058118 | 7/2004 |
| 2006/0105664 A1 | 5/2006 | Zafiroglu | WO | WO2004/058497 | 7/2004 |
| 2006/0183389 A1 | 8/2006 | Zafiroglu | WO | WO2004/059061 | 7/2004 |
| 2006/0225258 A1 | 10/2006 | Barker et al. | WO | WO2004/059117 | 7/2005 |
| 2007/0178273 A1 | 8/2007 | Provost et al. | WO | WO 2006/110575 | 10/2006 |
| 2008/0113152 A1 | 5/2008 | Provost et al. | WO | WO 2006/110598 | 10/2006 |
| 2008/0305291 A1 | 12/2008 | Nakaoka et al. | | | |
| 2008/0305704 A1 | 12/2008 | Provost et al. | | | |

FOREIGN PATENT DOCUMENTS

| | | |
|---|---|---|
| EP | 0 341 993 | 11/1989 |
| EP | 0 211 564 | 2/1992 |
| EP | 0 482 749 A1 | 4/1992 |
| EP | 0 325 473 | 3/1993 |
| EP | 0 604 731 | 7/1994 |
| EP | 0 765 616 A1 | 4/1997 |
| EP | 0 780 505 A2 | 6/1997 |
| EP | 0 598 085 | 7/1997 |
| EP | 0 597 075 | 4/1998 |
| EP | 0 882 828 A1 | 12/1998 |
| EP | 0 937 420 | 8/1999 |
| EP | 0 726 977 | 6/2000 |
| EP | 0 862 868 | 6/2001 |
| EP | 1 132 511 | 9/2001 |
| EP | 0 861 137 | 1/2002 |
| EP | 1 279 348 | 1/2003 |
| EP | 1279348 A1 * | 1/2003 |
| EP | 1 156 767 | 10/2004 |
| EP | 1 113 099 | 3/2006 |
| GB | 1228431 | 4/1971 |
| GB | 2 285 093 | 6/1995 |

OTHER PUBLICATIONS

Dilo, "Engineering Excellence in Needle Looms!", Hyperpunch—The Solution for Fine and Quality Fleeces, Synthetic Leather, Spunbondeds, Papermachine Felts!, date unknown (2 pages).

Purdy, Terry, Dilo Inc., Needle Punching Benefits from Elliptical Needle Paths, date unknown (13 pages).

U.S. Appl. No. 12/133,769, filed Jun. 5, 2008, Barker et al.

U.S. Appl. No. 12/133,945, filed Jun. 5, 2008, Provost et al.

Website: http://www.inda.org/pubs/c-papers/np00-toc.html. Inda.org, Needlepunch 2000 conference paper listing, retrieved Sep. 24, 2007. 2 Pages.

Narejo, D., et al, "Advances in Needlepunching", GFR, Jun./Jul. 2002, pp. 18-21.

"Drawing" Definition, Complete Textile Glossary. Celanese Acetate. 2001, 3 pages.

PCT International Search Report and Written Opinion from PCT/US2006/013180 dated Aug. 25, 2006.

PCT International Search Report and Written Opinion from PCT/US2008/065938 dated Nov. 11, 2008.

PCT International Search Report and Written Opinion from PCT/US2008/065944 dated Nov. 25, 2008.

* cited by examiner

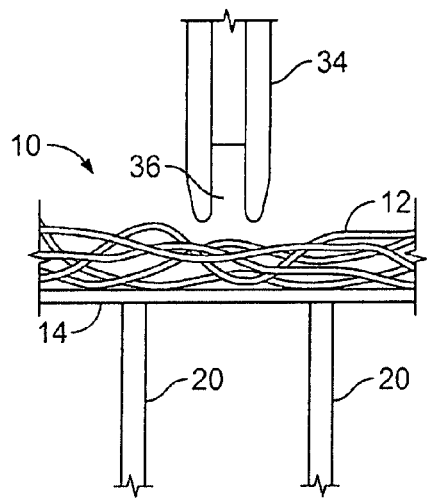
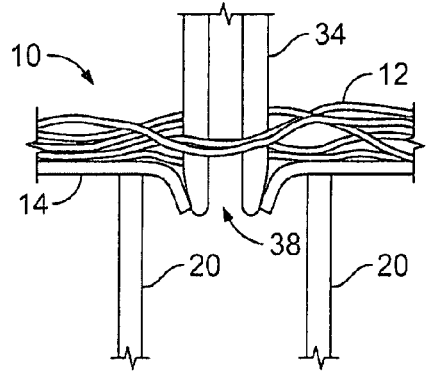
FIG. 2A                FIG. 2B
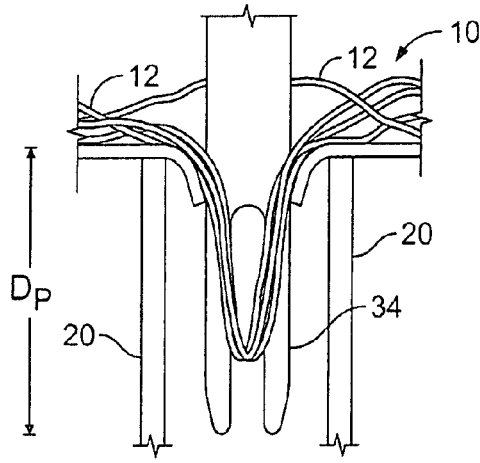
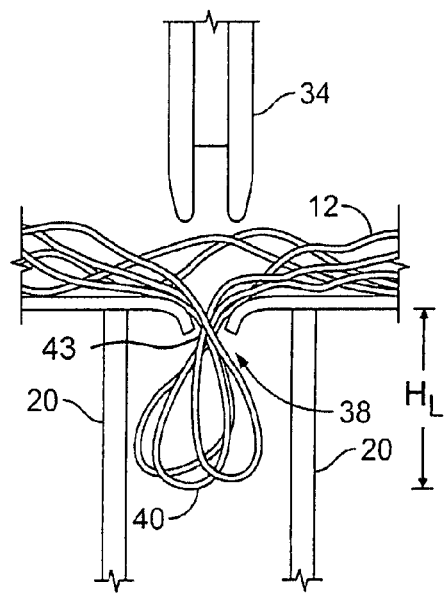
FIG. 2C                FIG. 2D

FORMING LOOP MATERIALS

CROSS-REFERENCE TO RELATED APPLICATIONS

This application is a continuation-in-part application of, and claims priority under 35 U.S.C. §120 to, U.S. application Ser. No. 10/728,138, filed on Dec. 3, 2003, now U.S. Pat. No. 7,156,937 and also claims priority under 35 U.S.C. § 119(e) to U.S. provisional application 60/430,731, filed on Dec. 3, 2002. The entire contents of both of these priority applications are incorporated herein by reference, as is set forth in their entirety.

TECHNICAL FIELD

This invention relates to loop materials, and more particularly to sheet-form materials bearing loops for touch fastening.

BACKGROUND

Touch fasteners are particularly desirable as fastening systems for lightweight, disposable garments, such as diapers. In an effort to provide a cost-effective loop material, some have recommended various alternatives to weaving or knitting, such as by needling a lightweight layer of fibers to form a light non-woven material that can then be stretched to achieve even lighter basis weight and cost efficiency, with the loop structures anchored by various binding methods, and subsequently adhered to a substrate. U.S. Pat. No. 6,329,016 teaches one such method, for example.

Inexpensive loop materials are desired, for touch fastening and other purposes, with particular characteristics suitable for various applications.

SUMMARY

The invention features, in several aspects, loop materials with discrete regions of loops.

In one aspect of the invention, a loop material for touch fastening includes: a flexible sheet-form substrate; and hook-engageable fibers secured individually and directly to the substrate. The fibers are disposed in discrete fastening regions of the substrate, leaving fiber-free substrate between adjacent fastening regions. In some cases, the loop material also includes discrete, spaced apart regions of fastener elements.

In some embodiments, the fibers extend through holes pierced through the substrate. In some cases, the fibers are fused to a surface of the substrate at discrete bonding locations within the fastening regions.

In some embodiments, the discrete fastening regions are surrounded by fiber-free substrate. In some of these embodiments, the discrete fastener regions are circular. In other embodiments, the discrete fastening regions include parallel lanes separated by the fiber-free substrate. In some of these other embodiments, the lanes are longitudinally continuous.

In some embodiments, the substrate includes a polymer film. In some embodiments, the substrate includes a scrim. In some embodiments, the substrate includes paper.

In some embodiments, the substrate has parting lines defining individual fastening products with each fastening product containing an undivided one of the discrete fastening regions.

In some embodiments, the fibers have strength, defined as tenacity times denier, of at least 8 grams.

In some embodiments, the fibers include bicomponent fibers having a core of one material and a sheath of another material, material of the sheaths of the bicomponent fibers binding fibers together.

In some embodiments, the loop material can have an overall weight of less than about 5 ounces per square yard (167 grams per square meter) (e.g. an overall weight of less than about 2 ounces per square yard (67 grams per square meter)).

In some cases, the loop material, in a continuous length, is spooled into roll form.

In another aspect of the invention, a method of forming a loop material for touch fastening includes: disposing loose, staple fibers on a front surface of a flexible, sheet-form substrate; and then securing the staple fibers to the substrate in only discrete regions of the substrate, forming a loop material having discrete fastening regions of secured, hook-engageable fibers, the fastening regions separated by fiber-free substrate.

In some embodiments, the method features carding and cross-lapping the fibers prior to disposing the fibers on the substrate. In some cases, the method also features heating the fibers from the front surface of the substrate after needling and prior to laminating.

In some embodiments, disposing the staple fibers on the substrate includes disposing fibers on a broad area of the front surface, and securing the staple fibers includes securing fibers to the substrate in the discrete regions while leaving unsecured fibers in other parts of the broad area. In these embodiments, the method also includes removing the unsecured fibers to expose fiber-free substrate. In other embodiments, disposing the staple fibers on the substrate includes disposing the fibers only in the discrete regions, leaving fiber-free substrate between the discrete regions.

In some embodiments, the staple fibers are disposed on the substrate in a layer of a total fiber weight of less than about 2 ounces per square yard (67 grams per square meter). In some cases, the staple fibers are disposed on the substrate in a layer of a total fiber weight of no more than about one ounce per square yard (34 grams per square meter). In some cases, the staple fibers are disposed on the substrate in a carded, unbonded state.

In some embodiments, securing the fibers to the substrate comprises laminating the fibers to the substrate by pressing the fibers against the substrate employing a bed of discrete pins that apply pressure to the substrate only at discrete points corresponding to the pins. In some cases, the fibers are loose and unconnected to the substrate until laminated. In some cases, securing the fibers to the substrate also includes, prior to laminating, needling the fibers through the substrate to form loop structures extending from a back surface of the substrate, and during laminating the pins press against the back surface of the substrate, such that the loop structures extend between the pins.

In some embodiments, securing the fibers to the substrate includes needling the fibers through the substrate to form loop structures extending from a back surface of the substrate. In some cases, the substrate is needled both in the fastening regions and in fiber-free regions between the fastening regions.

Advantageously, the fiber-free areas minimize the amount of fiber that is required to form the loop material, reducing cost and providing a very lightweight product. Furthermore, fibrous loops for fastening or other purposes can be formed only where desired. In this manner, preform materials can be produced, in which loops are predisposed in selected regions, and from which functional products can be manufactured without separately attaching loop materials to such regions.

The methods of forming such discrete regions of loop, as disclosed herein, can be particularly cost-effective in the production of loop materials suitable for touch fastening or other purposes.

The details of one or more embodiments of the invention are set forth in the accompanying drawings and the description below. Other features and advantages of the invention will be apparent from the description and drawings, and from the claims.

DESCRIPTION OF DRAWINGS

FIGS. 2A-2D are diagrammatic side views of stages of a needling step of the process of FIG. 1.

Like reference symbols in the various drawings indicate like elements.

DETAILED DESCRIPTION

Descriptions of loop products will follow a description of some methods of making loop products.

Figure 1:
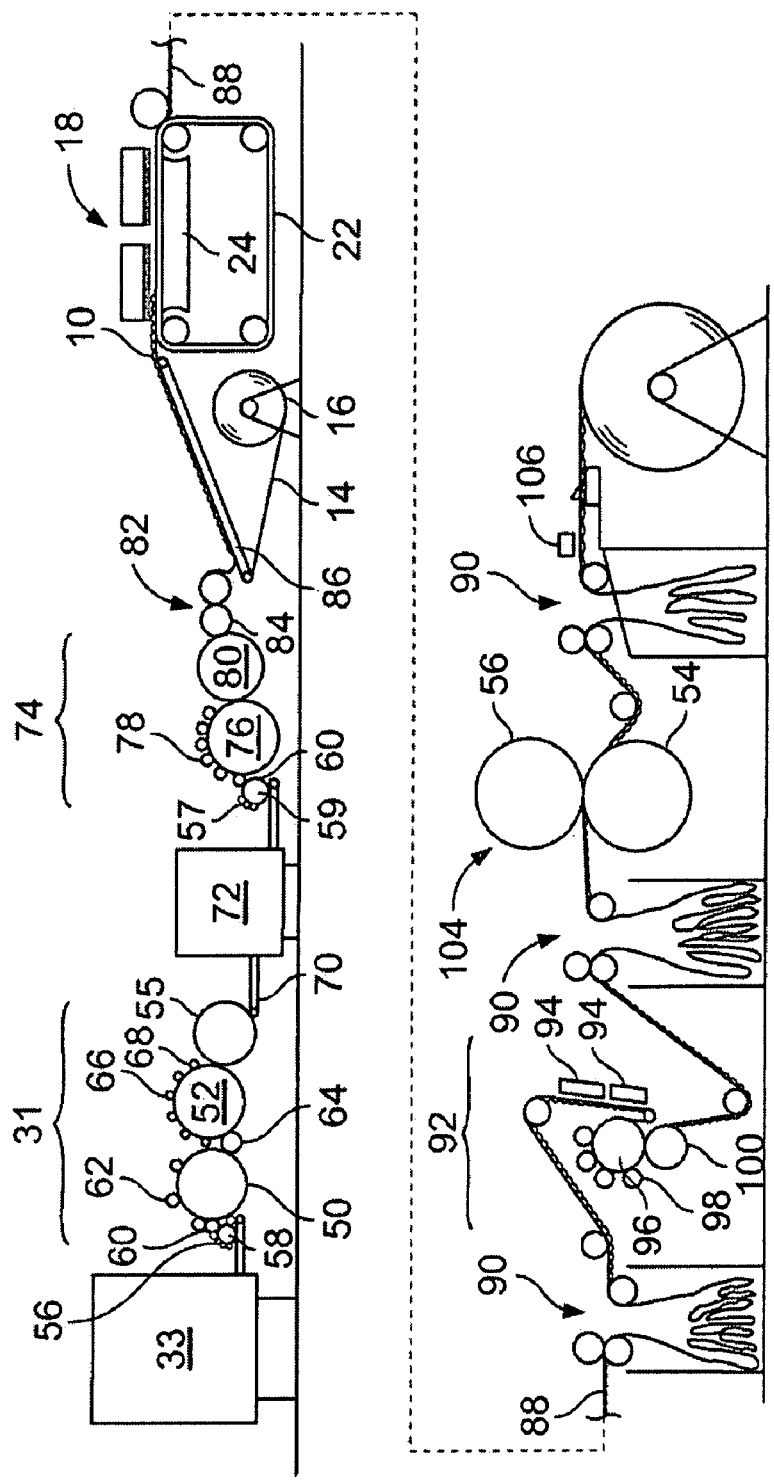
FIG. 1 is a diagrammatic view of a process for forming loop material.

FIG. 1 illustrates a machine and process for producing an inexpensive touch fastener loop product. Beginning at the upper left end of FIG. 1, a carded and cross-lapped layer of fibers 10 is created by two carding stages with intermediate cross-lapping. Weighed portions of staple fibers of different types are fed to the first carding station 31 by a card feeder 34. Card station 31 includes a 36-inch breast roll 50, a 60-inch breaker main 52, and a 50-inch breaker doffer 54. The first card feedroll drive includes 3-inch feedrolls 56 and a 3-inch cleaning roll on a 13-inch lickerin roll 58. An 8-inch angle stripper 60 transfers the fiber to breast roll 50. There are three 8-inch worker roll sets 62 on the breast roll, and a 16-inch breast doffer 64 feeds breaker main 52, against which seven 8-inch worker sets 66 and a flycatcher 68 run. The carded fibers are combed onto a conveyer 70 that transfers the single fiber layer into a cross-lapper 72. Before cross-lapping, the carded fibers still appear in bands or streaks of single fiber types, corresponding to the fibrous balls fed to carding station 31 from the different feed bins. Cross-lapping, which normally involves a 90-degree reorientation of line direction, overlaps the fiber layer upon itself and is adjustable to establish the width of fiber layer fed into the second carding station 74. In this example, the cross-lapper output width is set to approximately equal the width of the carrier into which the fibers will be needled. Cross-lapper 72 may have a lapper apron that traverses a floor apron in a reciprocating motion. The cross-lapper lays carded webs of, for example, about 80 inches (1.5 meters) width and about one-half inch (1.3 centimeters) thickness on the floor apron, to build up several layers of criss-crossed web to form a layer of, for instance, about 80 inches (1.5 meters) in width and about 4 inches (10 centimeters) in thickness, comprising four double layers of carded web. During carding, the fibers are separated and combed into a cloth-like mat consisting primarily of parallel fibers. With nearly all of its fibers extending in the carding direction, the mat has some strength when pulled in the carding direction but almost no strength when pulled in the carding cross direction, as cross direction strength results only from a few entanglements between fibers. During cross-lapping, the carded fiber mat is laid in an overlapping zigzag pattern, creating a mat 10 of multiple layers of alternating diagonal fibers. The diagonal layers, which extend in the carding cross direction, extend more across the apron than they extend along its length.

Cross-lapping the web before the second carding process provides several tangible benefits. For example, it enhances the blending of the fiber composition during the second carding stage. It also allows for relatively easy adjustment of web width and basis weight, simply by changing cross-lapping parameters.

Second carding station 74 takes the cross-lapped mat of fibers and cards them a second time. The feedroll drive consists of two 3-inch feed rolls and a 3-inch cleaning roll on a 13-inch lickerin 58, feeding a 60-inch main roll 76 through an 8-inch angle stripper 60. The fibers are worked by six 8-inch worker rolls 78, the last five of which are paired with 3-inch strippers. A 50-inch finisher doffer 80 transfers the carded web to a condenser 82 having two 8-inch condenser rolls 84, from which the web is combed onto a carrier sheet 14 fed from spool 16. The condenser increases the basis weight of the web from about 0.7 osy (ounce per square yard) to about 1.0 osy, and reduces the orientation of the fibers to remove directionality in the strength or other properties of the finished product.

The carrier sheet 14, such as polymer film or paper, may be supplied as a single continuous length, or as multiple, parallel strips. For particularly wide webs, it may be necessary or cost effective to introduce two or more parallel sheets, either adjacent or slightly overlapping. The parallel sheets may be unconnected or joined along a mutual edge. The carded, uniformly blended layer of fibers from condenser 82 is carried up conveyor 86 on carrier sheet 14 and into needling station 18. As the fiber layer enters the needling station, it has no stability other than what may have been imparted by carding and cross-lapping. In other words, the fibers are not pre-needled or felted prior to needling into the carrier sheet. In this state, the fiber layer is not suitable for spooling or accumulating prior to entering the needling station.

In needling station 18, the carrier sheet 14 and fiber are needle-punched from the fiber side. The needles are guided through a stripping plate above the fibers, and draw fibers through the carrier sheet 14 to form loops on the opposite side. During needling, the carrier sheet is supported on a bed of pins or bristles extending from a driven support belt or brush apron 22 that moves with the carrier sheet through the needling station. Alternatively, carrier sheet 14 can be supported on a screen or by a standard stitching plate (not shown). Reaction pressure during needling is provided by a stationary reaction plate 24 underlying apron 22. In this example, needling station 18 needles the fiber-covered carrier sheet 14 with an overall penetration density of about 80 to 160 punches per square centimeter. At this needling density and with a carrier sheet of a polypropylene film of a thickness of about 0.0005 inch (0.013 millimeter), we have found that 38 gauge forked tufting needles were small enough to not obliterate the film, leaving sufficient film interconnectivity that the film continued to exhibit some dimensional stability within its plane. With the same parameters, larger 30 gauge needles essentially segmented the film into small, discrete pieces entangled within the fibers. During needling, the thickness of the carded fiber layer only decreases by about half, as compared with felting processes in which the fiber layer thickness decreases by one or more orders of magnitude. As fiber basis weight decreases, needling density may need to be increased.

The needling station 18 may be a "structuring loom" configured to subject the fibers and carrier web to a random velouring process. Thus, the needles penetrate a moving bed of bristles arranged in an array (brush apron 22). The brush apron may have a bristle density of about 2000 to 3000 bristles per square inch (310 to 465 bristles per square centimeter), e.g., about 2570 bristles per square inch (400 per square centimeter). The bristles are each about 0.018 inch (0.46 millimeter) in diameter and about 20 millimeters long, and are preferably straight. The bristles may be formed of any suitable material, for example 6/12 nylon. Suitable brushes may be purchased from Stratosphere, Inc., a division of Howard Brush Co., and retrofitted onto DILO and other random velouring looms. Generally, the brush apron moves at the desired line speed.

Alternatively, other types of structuring looms may be used, for example those in which the needles penetrate into a plurality of lamella or lamellar disks.

FIGS. 2A through 2D sequentially illustrate the formation of a loop structure by needling. As a forked needle enters the fiber mat 10 (FIG. 2A), some individual fibers 12 will be captured in the cavity 36 in the forked end of the needle. As needle 34 pierces film 14 (FIG. 2B), these captured fibers 12 are drawn with the needle through the hole 38 formed in the film to the other side of the film. As shown, film 14 remains generally supported by pins 20 through this process, the penetrating needle 34 entering a space between adjacent pins. Alternatively, film 14 can be supported by a screen or stitching plate (not shown) that defines holes aligned with the needles. As needle 34 continues to penetrate (FIG. 2C), tension is applied to the captured fibers, drawing mat 10 down against film 14. In this example, a total penetration depth "$D_p$" of about 5.0 millimeters, as measured from the entry surface of film 14, was found to provide a well-formed loop structure without overly stretching fibers in the remaining mat. Excessive penetration depth can draw loop-forming fibers from earlier-formed tufts, resulting in a less robust loop field. Penetration depths of 2 and 7 millimeters also worked in this example, although the 5.0 millimeter penetration is presently preferred. When needle 34 is retracted (FIG. 2D), the portions of the captured fibers 12 carried to the opposite side of the carrier web remain in the form of a plurality of individual loops 40 extending from a common trunk 43 trapped in film hole 38. As shown, residual stresses in the film 14 around the hole, acting to try to restore the film to its planar state, can apply a slight pressure to the fibers in the hole, helping to secure the base of the loop structure. The film can also help to resist tension applied to the fiber remaining on the mat side of the film that would tend to pull the loops back through the hole. The final loop formation preferably has an overall height "$H_L$" of about 0.040 to 0.090 inch (1.0 to 2.3 millimeters), for engagement with the size of male fastener elements commonly employed on disposable garments and such.

Advance per stroke is limited due to a number of constraints, including needle deflection and potential needle breakage. Thus, it may be difficult to accommodate increases in line speed and obtain an economical throughput by adjusting the advance per stroke. As a result, the holes pierced by the needles may become elongated, due to the travel of the carrier sheet while the needle is interacting with the carrier sheet (the "dwell time"). This elongation is generally undesirable, as it reduces the amount of support provided to the base of each of the loop structures by the surrounding substrate, and may adversely affect resistance to loop pull-out. Moreover, this elongation will tend to reduce the mechanical integrity of the carrier film due to excessive drafting, i.e., stretching of the film in the machine direction and corresponding shrinkage in the cross-machine direction.

Figure 2E:
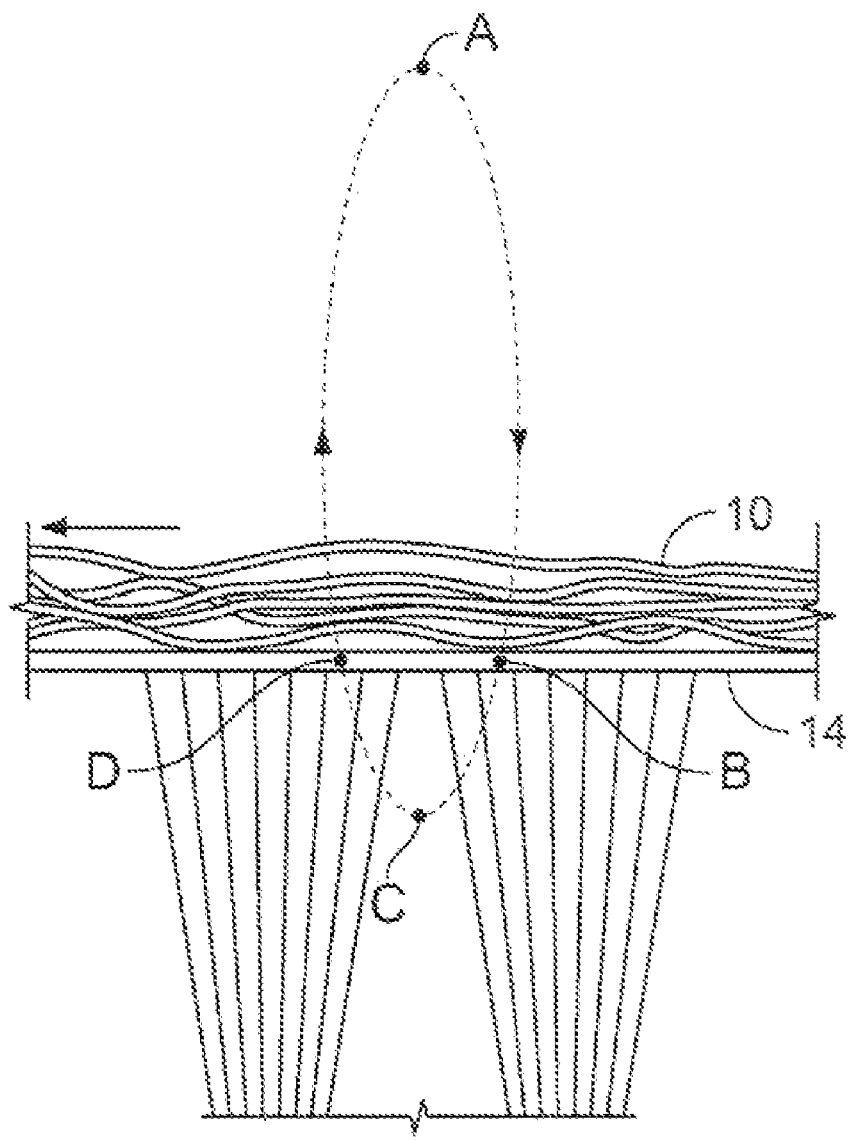
FIG. 2E is a diagrammatic side view showing an elliptical path that may be followed by the needle during needling.

Elongation of the holes may be reduced or eliminated by causing the needles to travel in a generally elliptical path, viewed from the side. This elliptical path is shown schematically in FIG. 2E. Referring to FIG. 2E, each needle begins at a top "dead" position A, travels downward to pierce the film (position B) and, while it remains in the film (from position B through bottom "dead" position C to position D), moves forward in the machine direction. When the needle has traveled upward sufficiently for its tip to have exited the pierced opening (position D), it continues to travel upward, free of the film, while also returning horizontally (opposite to the machine direction) to its normal, rest position (position A), completing the elliptical path. This elliptical path of the needles is accomplished by moving the entire needle board simultaneously in both the horizontal and vertical directions. Needling in this manner is referred to herein as "elliptical needling." Needling looms that perform this function are available from DILO System Group, Eberbach, Germany, under the tradename "HYPERPUNCH Systems."

During elliptical needling, the horizontal travel of the needle board is preferably roughly equivalent to the distance that the film advances during the dwell time. The horizontal travel is a function of needle penetration depth, vertical stroke length, carrier film thickness, and advance per stroke. Generally, at a given value of needle penetration and film thickness, horizontal stroke increases with increasing advance per stroke. At a fixed advance per stroke, the horizontal stroke generally increases as depth of penetration and web thickness increases.

For example, for a polypropylene film having a thickness of 0.0005 inch (so thin that it is not taken into account), a loom outfeed of 18.9 m/min, an effective needle density of 15,006 needles/meter, a vertical stroke of 35 mm, a needle penetration of 5.0 mm, and a headspeed of 2,010 strokes/min, the preferred horizontal throw (i.e., the distance between points B and D in FIG. 2E) would be 3.3 mm, resulting in an advance per stroke of 9.4 mm.

Using elliptical needling, it may be possible to obtain line speeds 30 ypm (yards/minute) or mpm (meters/minute) or greater, e.g., 50 ypm or mpm, for example 60 ypm. Such speeds may be obtained with minimal elongation of the holes, for example the length of the holes in the machine direction may be less than 20% greater than the width of the holes in the cross-machine direction, preferably less than 10% greater and in some instances less than 5% greater.

For needling longitudinally discontinuous regions of the material, such as to create discrete loop regions as discussed further below, the needle boards can be populated with needles only in discrete regions, and the needling action paused while the material is indexed through the loom between adjacent loop regions. Effective pausing of the needling action can be accomplished by altering the penetration depth of the needles during needling, including to needling depths at which the needles do not penetrate the carrier sheet. Such needle looms are available from FEHRER AG in Austria, for example. Alternatively, means can be implemented to selectively activate smaller banks of needles within the loom according to a control sequence that causes the banks to be activated only when and where loop structures are desired. Lanes of loops can be formed by a needle loom with lanes of needles separated by wide, needle-free lanes.

In the example illustrated, the needled product 88 leaves needling station 18 and brush apron 22 in an unbonded state, and proceeds to a lamination station 92. If the needling step was performed with the carrier sheet supported on a bed of rigid pins, lamination can be performed with the carrier sheet still carried on the bed of pins. Prior to the lamination station, the web passes over a gamma gage (not shown) that provides a rough measure of the mass per unit area of the web. This measurement can be used as feedback to control the upstream carding and cross-lapping operations. The web is stable enough at this stage to be accumulated in an accumulator 90 between the needling and lamination stations. As known in the art, accumulator 90 is followed by a spreading roll (not shown) that spreads and centers the web prior to entering the next process. Prior to lamination, the web may also pass through a coating station (not shown) in which a binder is applied to enhance lamination. In lamination station 92, the web first passes by one or more infrared heaters 94 that preheat the fibers and/or carrier sheet from the side opposite the loops. In products relying on bicomponent fibers for bonding, heaters 94 preheat and soften the sheaths of the bicomponent fibers. In one example, the heater length and line speed are such that the web spends about four seconds in front of the heaters. Just downstream of the heaters is a web temperature sensor (not shown) that provides feedback to the heater control to maintain a desired web exit temperature. For lamination, the heated web is trained about a hot can 96 against which four idler card cloth-covered rolls 98 of five inch (13 centimeters) solid diameter (excluding the card cloth), and a driven, rubber, card cloth-covered roll 100 of 18 inch (46 centimeters) solid diameter, rotate under controlled pressure. The pins of the card cloth rolls 98,100 thus press the web against the surface of hot can 96 at discrete pressure points, thus bonding the fibers at discrete locations without crushing other fibers, generally between the bond points, that remain exposed and open for engagement by hooks. For many materials, the bonding pressure between the card cloth rolls and the hot can is quite low, in the range of 1-10 pounds per square inch (70-700 grams per square centimeter) or less. The surface of hot can 96 is maintained at a temperature of about 306 degrees Fahrenheit (150 degrees Celsius) for one example employing bicomponent polyester fiber and polypropylene film, to just avoid melting the polypropylene film. The hot can 96 can have a compliant outer surface, or be in the form of a belt. As an alternative to roller nips, a flatbed fabric laminator (not shown) can be employed to apply a controlled lamination pressure for a considerable dwell time. Such flatbed laminators are available from Glenro Inc. in Paterson, N.J. In some applications, the finished loop product is passed through a cooler (not shown) prior to embossing.

The pins extending from card cloth-covered rolls 98,100 are arranged in an array of rows and columns, with a pin density of about 200 and 350 pins per square inch (31 to 54 pins per square centimeter) in a flat state, preferred to be between about 250 to 300 pins per square inch (39 to 47 pins per square centimeter). The pins are each about 0.020 inch (0.5 millimeter) in diameter, and are preferably straight to withstand the pressure required to laminate the web. The pins extend from a backing about 0.25 inch (6.4 millimeters) in thickness. The backing is of two layers of about equal thickness, the lower layer being of fibrous webbing and the upper layer being of rubber. The pins extend about 0.25 inch (6.4 millimeters) from the rubber side of the backing. Because of the curvature of the card cloth rolls, the effective density of the pin tips, where lamination occurs, is lower than that of the pins with the card cloth in a flat state. A flat state pin density of 200 to 350 pins per square inch (31 to 54 pins per square centimeter) equates to an effective pin density of only 22 to 38 pins per square centimeter on idler rolls 98, and 28 to 49 pins per square centimeter on driven rubber roll 100. In most cases, it is preferable that the pins not penetrate the carrier sheet during bonding, but that each pin provide sufficient support to form a robust bond point between the fibers. In a non-continuous production method, such as for preparing discrete patches of loop material, a piece of carrier sheet 14 and a section of fiber mat 12 may be layered upon a single card cloth, such as are employed for carding webs, for needling and subsequent bonding, prior to removal from the card cloth.

Figure 3:
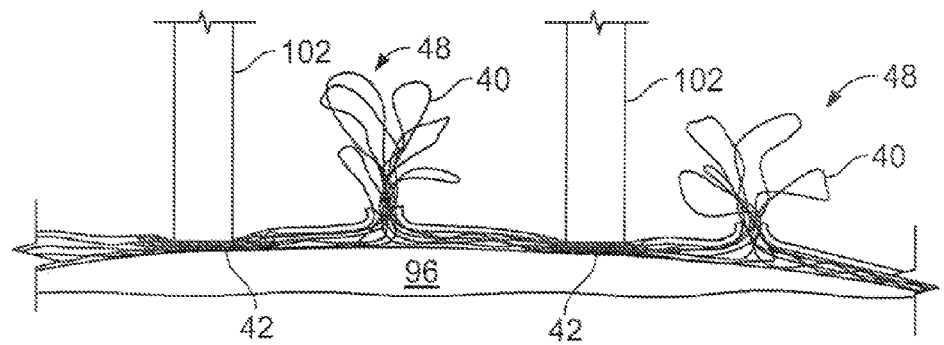
FIG. 3 is an enlarged diagrammatic view of a lamination nip through which the loop material passes during the process of FIG. 1.

FIG. 3 is an enlarged view of the nip between hot can 96 and one of the card cloth rolls. As discussed above, due to the curvature of the card cloth rolls, their pins 102 splay outward, such that the effective pin density at the hot can is lower than that of the card cloth in a planar state. The pins contact the carrier sheet (or its remnants, depending on needling density) and fuse underlying fibers to each other and/or to material of the carrier sheet, forming a rather solid mass 42 of fused material in the vicinity of the pin tip, and a penumbral area of fused but distinct fibers surrounding each pin. The laminating parameters can be varied to cause these penumbral, partially fused areas to be overlapped if desired, creating a very strong, dimensionally stable web of fused fibers across the non-working side of the loop product that is still sufficiently flexible for many uses. Alternatively, the web can be laminated such that the penumbral areas are distinct and separate, creating a looser web. For most applications the fibers should not be continuously fused into a solid mass across the back of the product, in order to retain a good hand and working flexibility. The number of discrete fused areas per unit area of the bonded web is such that staple fibers with portions extending through holes to form engageable loops 40 that have other portions, such as their ends, secured in one or more of such fused areas 42, such that the fused areas are primarily involved in anchoring the loop fibers against pullout from hook loads. Whether the welds are discrete points or an interconnected grid, this further secures the fibers, helping to strengthen the loop structures 48. The laminating occurs while the loop structures 48 are safely disposed between pins 102, such that no pressure is applied to crush the loops during bonding. Protecting the loop structures during lamination significantly improves the performance of the material as a touch fastener, as the loop structures remain extended from the base for hook engagement.

If desired, a backing sheet (not shown) can be introduced between the hot can and the needled web, such that the backing sheet is laminated over the back surface of the loop product while the fibers are bonded under pressure from the pins of apron 22.

Figure 7B:
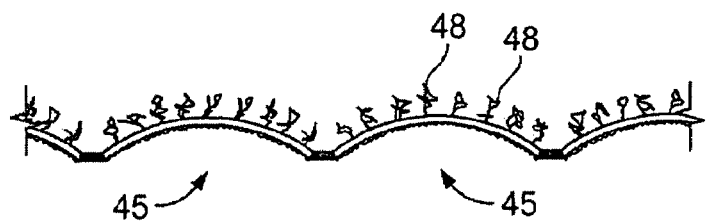
FIG. 7B is a highly enlarged diagrammatic view of an embossed loop material having convex regions.

Referring back to FIG. 1, from lamination station 92 the laminated web moves through another accumulator 90 to an embossing station 104, where a desired pattern of locally raised regions is embossed into the web between two counter-rotating embossing rolls. In some cases, the web may move directly from the laminator to the embossing station, without accumulation, so as to take advantage of any latent temperature increase caused by lamination. The loop side of the bonded loop product is embossed with a desired embossing pattern prior to spooling. In this example the loop product is passed through a nip between a driven embossing roll 54 and a backup roll 56. The embossing roll 54 has a pattern of raised areas that permanently crush the loop formations against the carrier sheet, and may even melt a proportion of the fibers in those areas. Embossing may be employed simply to enhance the texture or aesthetic appeal of the final product. In some cases, roll 56 has a pattern of raised areas that mesh with dimples in roll 54, such that embossing results in a pattern of raised hills or convex regions on the loop side, with corresponding concave regions 45 (FIG. 7B) on the non-working side of the product, such that the embossed product has a greater effective thickness than the pre-embossed product. Additionally, as shown in FIG. 7B, embossing presents the loop structures 48 or otherwise engageable fiber portions at different angles to a mating field of hooks, for better engagement. More details of a suitable embossing pattern are discussed below with respect to FIGS. 7 and 7A.

The embossed web then moves through a third accumulator 90, past a metal detector 106 that checks for any broken needles or other metal debris, and then is slit and spooled for storage or shipment. During slitting, edges may be trimmed and removed, as can any undesired carrier sheet overlap region necessitated by using multiple parallel strips of carrier sheet.

We have found that, using the process described above, a useful loop product may be formed with relatively little fiber 12. In one example, mat 10 has a basis weight of only about 1.0 osy (33 grams per square meter). Fibers 12 are drawn and crimped polyester fibers, 3 to 6 denier, of about a four-inch (10 centimeters) staple length, mixed with crimped bicomponent polyester fibers of 4 denier and about two-inch (5 centimeters) staple length. The ratio of fibers may be, for example, 80 percent solid polyester fiber to 20 percent bicomponent fiber. In other embodiments, the fibers may include 15 to 30 percent bicomponent fibers. The preferred ratio will depend on the composition of the fibers and the processing conditions. Generally, too little bicomponent fiber may compromise loop anchoring, due to insufficient fusing of the fibers, while too much bicomponent fiber will tend to increase cost and may result in a stiff product and/or one in which some of the loops are adhered to each other. The bicomponent fibers are core/sheath drawn fibers consisting of a polyester core and a copolyester sheath having a softening temperature of about 110 degrees Celsius, and are employed to bind the solid polyester fibers to each other and the carrier.

In this example, both types of fibers are of round cross-section and are crimped at about 7.5 crimps per inch (3 crimps per centimeter). Suitable polyester fibers are available from INVISTA of Wichita, Kans., (www.invista.com) under the designation Type 291. Suitable bicomponent fibers are available from INVISTA under the designation Type 254. As an alternative to round cross-section fibers, fibers of other cross-sections having angular surface aspects, e.g. fibers of pentagon or pentalobal cross-section, can enhance knot formation during needling.

Loop fibers with tenacity values of at least 2.8 grams per denier have been found to provide good closure performance, and fibers with a tenacity of at least 5 or more grams per denier (preferably even 8 or more grams per denier) are even more preferred in many instances. In general terms for a loop-limited closure, the higher the loop tenacity, the stronger the closure. The polyester fibers of mat 10 are in a drawn, molecular oriented state, having been drawn with a draw ratio of at least 2:1 (i.e., to at least twice their original length) under cooling conditions that enable molecular orientation to occur, to provide a fiber tenacity of about 4.8 grams per denier.

The loop fiber denier should be chosen with the hook size in mind, with lower denier fibers typically selected for use with smaller hooks. For low-cycle applications for use with larger hooks (and therefore preferably larger diameter loop fibers), fibers of lower tenacity or larger diameter may be employed.

For many applications, particularly products where the hook and loop components will be engaged and disengaged more than once ("cycled"), it is desirable that the loops have relatively high strength so that they do not break or tear when the fastener product is disengaged. Loop breakage causes the loop material to have a "fuzzy," damaged appearance, and widespread breakage can deleteriously effect re-engagement of the fastener.

Loop strength is directly proportional to fiber strength, which is the product of tenacity and denier. Fibers having a fiber strength of at least 6 grams, for example at least 10 grams, provide sufficient loop strength for many applications. Where higher loop strength is required, the fiber strength may be higher, e.g., at least 15. Strengths in these ranges may be obtained by using fibers having a tenacity of about 2 to 7 grams/denier and a denier of about 1.5 to 5, e.g., 2 to 4. For example, a fiber having a tenacity of about 4 grams/denier and a denier of about 3 will have a fiber strength of about 12 grams.

Other factors that affect engagement strength and cycling are the geometry of the loop structures, the resistance of the loop structures to pull-out, and the density and uniformity of the loop structures over the surface area of the loop product. The first two of these factors are discussed above. The density and uniformity of the loop structures is determined in part by the coverage of the fibers on the carrier sheet. In other words, the coverage will affect how many of the needle penetrations will result in hook-engageable loop structures. Fiber coverage is indicative of the length of fiber per unit area of the carrier sheet, and is calculated as follows:

Fiber coverage (meters per square meter)=Basis Weight/Denier×9000

Thus, in order to obtain a relatively high fiber coverage at a low basis weight, e.g., less than 2 osy, it is desirable to use relatively low denier (i.e., fine) fibers. However, the use of low denier fibers will require that the fibers have a higher tenacity to obtain a given is 5 fiber strength, as discussed above. Higher tenacity fibers are generally more expensive than lower tenacity fibers, so the desired strength, cost and weight characteristics of the product must be balanced to determine the appropriate basis weight, fiber tenacity and denier for a particular application. It is generally preferred that the fiber layer of the loop product have a calculated fiber coverage of at least 50,000, preferably at least 90,000, and more preferably at least 100,000.

To produce loop materials having a good balance of low cost, light weight and good performance, it is generally preferred that the basis weight be less than 2.0 osy, e.g., 1.0 to 2.0 osy, and the coverage be about 50,000 to 200,000.

Various synthetic or natural fibers may be employed. In some applications, wool and cotton may provide sufficient fiber strength. Presently, thermoplastic staple fibers which have substantial tenacity are preferred for making thin, low-cost loop product that has good closure performance when paired with very small molded hooks. For example, polyolefins (e.g., polypropylene or polyethylene), polyesters (e.g., polyethylene terephthalate), polyamides (e.g., nylon), acrylics and mixtures, alloys, copolymers and co-extrusions thereof are suitable. Polyester is presently preferred. Fibers having high tenacity and high melt temperature may be mixed with fibers of a lower melt temperature resin. For a product having some electrical conductivity, a small percentage of metal fibers may be added. For instance, loop products of up to about 5 to 10 percent fine metal fiber, for example, may be advantageously employed for grounding or other electrical applications.

In one example, mat 10 is laid upon a blown polyethylene film 14, such as is available for bag-making and other packaging applications. Film 14 has a thickness of about 0.002 inch (0.05 millimeter). Even thinner films may be employed, with good results. Other suitable films include polyesters, polypropylenes, EVA, and their copolymers. Other carrier web materials may be substituted for film 14 for particular applications. For example, fibers may be needle-punched into paper, scrim, or fabrics such as non-woven, woven or knit materials, for example lightweight cotton sheets. If paper is used, it may be pre-pasted with an adhesive on the fiber side to help bond the fibers and/or a backing layer to the paper.

Still referring to FIG. 1, in some cases a wire screen is used in place of both the bed of pins or bristles 20 and driven support belt 22, for an analogous needling process. The wires define openings through which the needle passes as it draws fibers 12 through the carrier sheet 14. Suitable screens can be made from materials including bronze, copper, brass, and stainless steel. We have found that screens made of brass wire with a nominal diameter of between about 0.02 and 0.03 inch (0.5 and 0.8 millimeter) or, more preferably, between about 0.023 and 0.028 inch (0.6 and 0.7 millimeter), are resilient without being too stiff. Screens having openings with a nominal width of between about 0.05 and 0.2 inch (1.3 and 5.1 millimeter) or, more preferably, between about 0.06 and 0.1 inch (1.5 and 2.5 millimeter) are appropriate for this purpose. Such screens are available from McMaster-Carr Supply Co. of Elmhurst, Ill. under the designation 9223T41.

Figure 4:
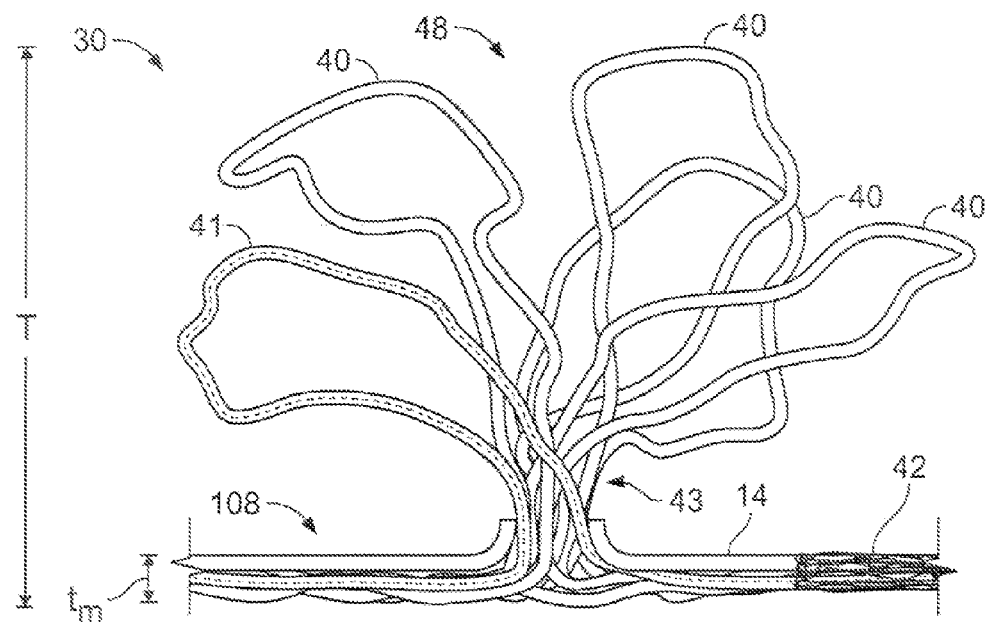
FIG. 4 is a highly enlarged diagrammatic view of a loop structure formed by needling with fork needles through film.

FIG. 4 is an enlarged view of a loop structure 48 containing multiple loops 40 extending from a common trunk 43 through a hole in film 14, as formed by the above-described method. As shown, loops 40 stand proud of the underlying film, available for engagement with a mating hook product, due at least in part to the vertical stiffness of trunk 43 of each formation, which is provided both by the constriction of the film material about the hole and the anchoring of the fibers to each other and the film. This vertical stiffness acts to resist permanent crushing or flattening of the loop structures, which can occur when the loop material is spooled or when the finished product to which the loop material is later joined is compressed for packaging. Resiliency of the trunk 43, especially at its juncture with the base, enables structures 48 that have been "toppled" by heavy crush loads to right themselves when the load is removed. The various loops 40 of formation 48 extend to different heights from the film, which is also believed to promote fastener performance. Because each formation 48 is formed at a site of a penetration of film 14 during needling, the density and location of the individual structures are very controllable. Preferably, there is sufficient distance between adjacent structures so as to enable good penetration of the field of formations by a field of mating male fastener elements (not shown). Each of the loops 40 is of a staple fiber whose ends are disposed on the opposite side of the carrier sheet, such that the loops are each structurally capable of hook engagement. One of the loops 40 in this view is shown as being of a bicomponent fiber 41. The material of the high-tenacity fibers may be selected to be of a resin with a higher melt temperature than the film. After laminating, the film and fibers become permanently bonded together at discrete points 42 corresponding to the distal ends of pins 20.

Because of the relatively low amount of fibers remaining in the mat, together with the thinness of the carrier sheet and any applied backing layer, mat 108 can have a thickness "$t_m$" of only about 0.008 inch (0.2 millimeters) or less, preferably less than about 0.005 inch, and even as low as about 0.001 inch (0.025 millimeter) in some cases. The carrier film 14 has a thickness of less than about 0.002 inch (0.05 millimeter), preferably less than about 0.001 inch (0.025 millimeter) and even more preferably about 0.0005 inch (0.013 millimeter). The finished loop product 30 has an overall thickness "T" of less than about 0.15 inch (3.7 millimeters), preferably less than about 0.1 inch (2.5 millimeters), and in some cases less than about 0.05 inch (1.3 millimeter). The overall weight of the loop fastener product, including carrier sheet, fibers and fused binder (an optional component, discussed below), is preferably less than about 5 ounces per square yard (167 grams per square meter). For some applications, the overall weight is less than about 2 ounces per square yard (67 grams per square meter), or in one example, about 1.35 ounces per square yard (46 grams per square meter).

Figure 4A:
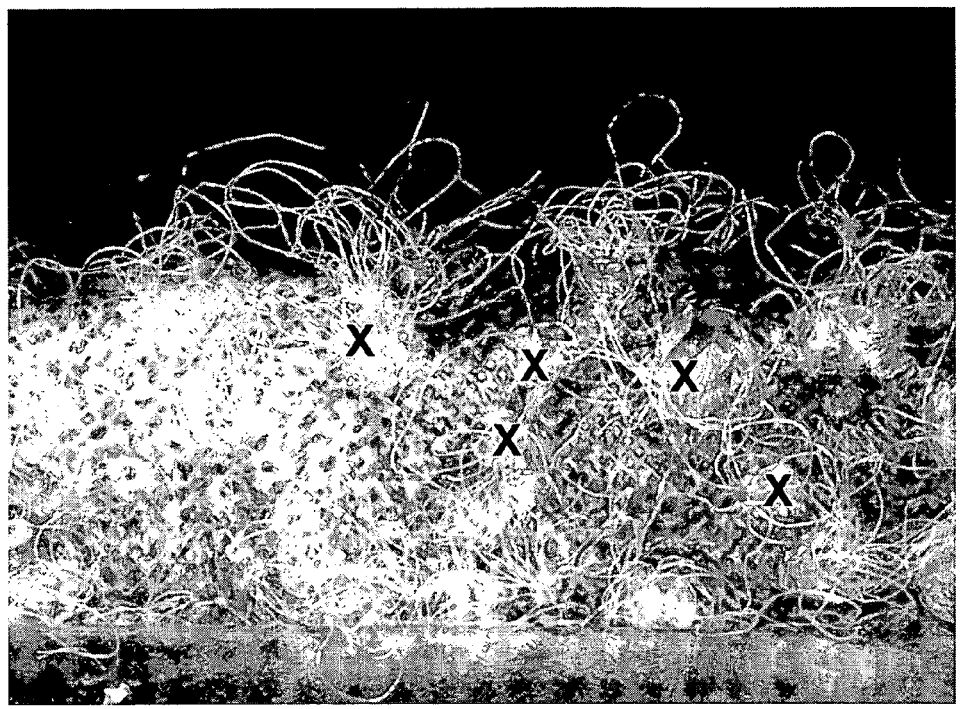
FIG. 4A is an enlarged photograph of a rolled edge of a loop product formed by needling with fork needles through film, showing several discrete loop structures.
Figure 4B:
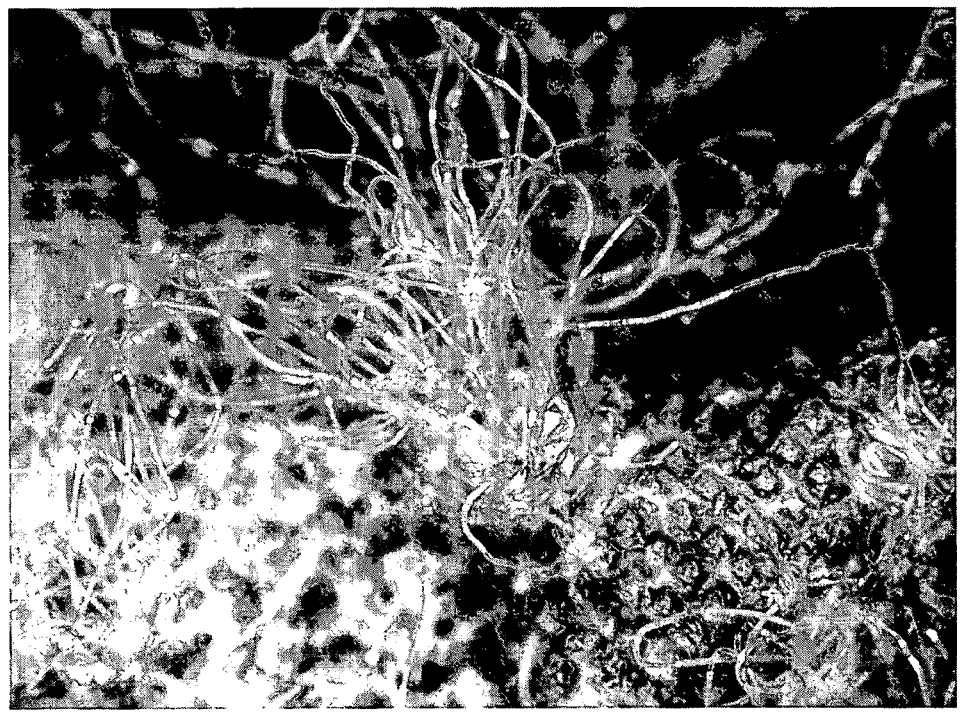
FIG. 4B is a highly enlarged photograph of one of the loop structures shown in FIG. 4A.

FIG. 4A is an enlarged photograph of a loop product formed by needling fibers through a film with fork needles. The view is taken toward a folded edge of the product, so as to spread out the loop structures for increased visibility. Five of the loop structures shown in the photograph have been marked with an 'X'. The surface of the film is clearly visible between the loop structures, each of which contains many individual loops emanating from a common trunk, as shown in FIG. 4B, an enlarged view of a single one of the loop structures. In FIG. 4B, light is clearly seen reflected at the base of the loop structure from film that has been raised about the hole during piercing, and that subsequently bears against the loop fibers in the hole, stiffening the trunk of the loop structure. An outline of the raised portion of film is shown on the photograph.

Figure 4C:
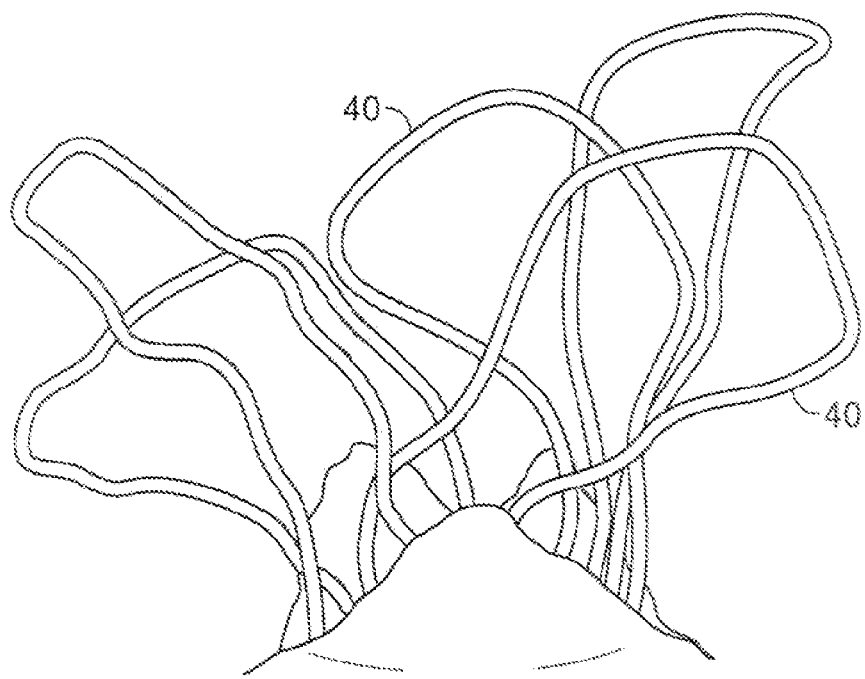
FIG. 4C illustrates a loop structure formed by needling with crown needles through polyester film.

Fork needles tend to produce the single-trunk structures as shown in FIG. 4, which we call 'loop trees.' Crown needles, by contrast, tend to create more of a 'loop bush' structure, as illustrated in FIG. 4C, particularly in film carrier sheets. As the barbs of crown needles go through the film, they are more likely to tear the film, perhaps due to increased notch sensitivity. In polyester films, such crown needle film fracturing limits the practical maximum punch density. We have not seen such fracturing in polyethylene, but did observe barb notching. In either case, the film hole created by a crown needle doesn't tend to create the 'turtleneck' effect as in FIG. 4, with the result that the fibers passing through the film are not as securely supported. Well-supported loop trees are more able to resist crushing, such as from spooling of the loop material, than less-supported bush structures. Fork needles also tend to create a field of loop structures of more uniform height, whereas felting needles with multiple barb heights tend to create loop structures of more varying loop height. Furthermore, as fork needles wear, they tend to carry more, rather than fewer, loops. Teardrop needles may also be employed, and may reduce the tendency to tear off small 'chads' of film that can be formed by fork needles.

Figure 5:
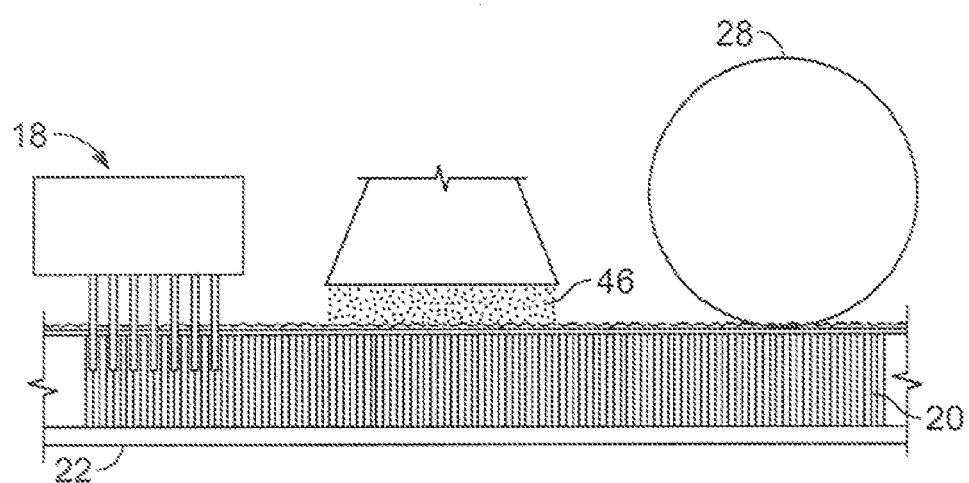
FIG. 5 is a diagrammatic view showing an alternative lamination step utilizing a powder-form binder.

Referring next to FIG. 5, in an alternative lamination step a powdered binder 46 is deposited over the fiber side of the needle-punched film and then fused to the film by roll 28 or a flatbed laminator. For example, a polyethylene powder with a nominal particle size of about 20 microns can be sprinkled over the fiber-layered polyethylene film in a distribution of only about 0.5 ounces per square yard (17 grams per square meter). Such powder is available in either a ground, irregular shape or a generally spherical form from Equistar Chemicals LP in Houston, Tex. Preferably, the powder form and particle size are selected to enable the powder to sift into interstices between the fibers and contact the underlying film. It is also preferable, for many applications, that the powder be of a material with a lower melt temperature than the loop fibers, such that during bonding the fibers remain generally intact and the powder binder fuses to either the fibers or the carrier web. In either case, the powder acts to mechanically bind the fibers to the film in the vicinity of the supporting pins and anchor the loop structures. In sufficient quantity, powder 46 can also form at least a partial backing in the finished loop product, for permanently bonding the loop material onto a compatible substrate. Other powder materials, such as polypropylene or an EVA resin, may also be employed for this purpose, with appropriate carrier web materials, as can mixtures of different powders.

Figure 6:
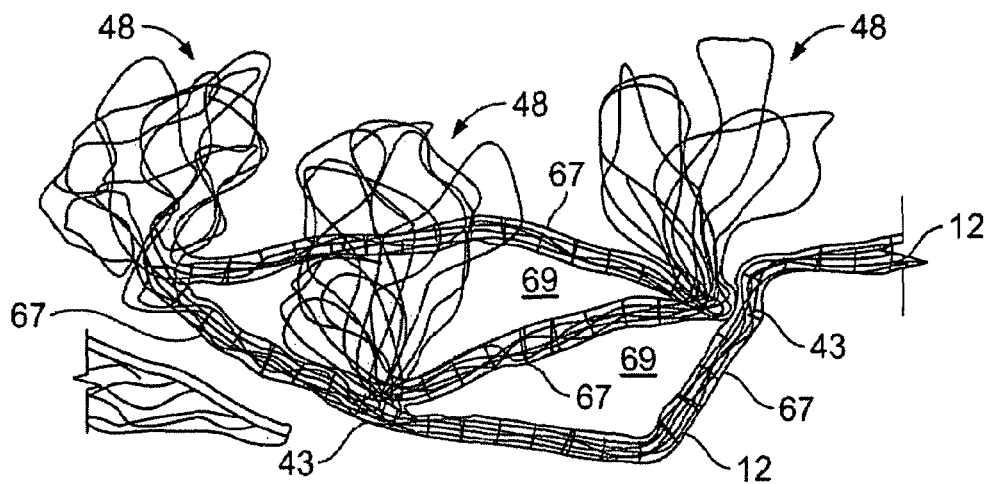
FIG. 6 is a highly enlarged diagrammatic view of a loop material according to an embodiment in which the carrier film is substantially disintegrated during needling.

Referring back to FIG. 1, in some cases the needling parameters (e.g., needle size, needling density) can be selected to cause the carrier web 14 to be practically disintegrated during needling. While this is undesirable for some applications, we have found that such a structure is advantageous for other uses. For example, in one case a fiber-covered 0.002 inch (0.05 millimeter) polyethylene film was needled with 30 gauge forked needles to a penetration density of 250 penetrations per square centimeter, resulting in a structure as shown in FIG. 6, in which the fibers 12 themselves formed practically the only connectivity within the needled sheet. The film itself remained in the form of discrete portions 69 separated by cracks 67 extending between adjacent loop trunks 43. This structure was sufficiently dimensionally stable to be laminated to a stretchable backing film, such as a polypropylene or polyethylene film available from Tredegar Film Products in Richmond, Va. During lamination, the discrete portions 69 of carrier film bonded to the stretchable backing, further anchoring the bases of the loop structures while permitting the final loop product to be elastically stretchable within its plane.

A pre-printed film or paper may be employed as the carrier web to provide graphic images visible from the loop side of the finished product. The small bonding spots and the low density of fiber remaining in the mat generally do not significantly detract from the visibility of the image. This can be advantageous, for example, for loop materials to be used on children's products, such as disposable diapers. In such cases, child-friendly graphic images can be provided on the loop material that is permanently bonded across the front of the diaper chassis to form an engagement zone for the diaper tabs. The image can be pre-printed on either surface of an otherwise transparent carrier film.

Figure 7:
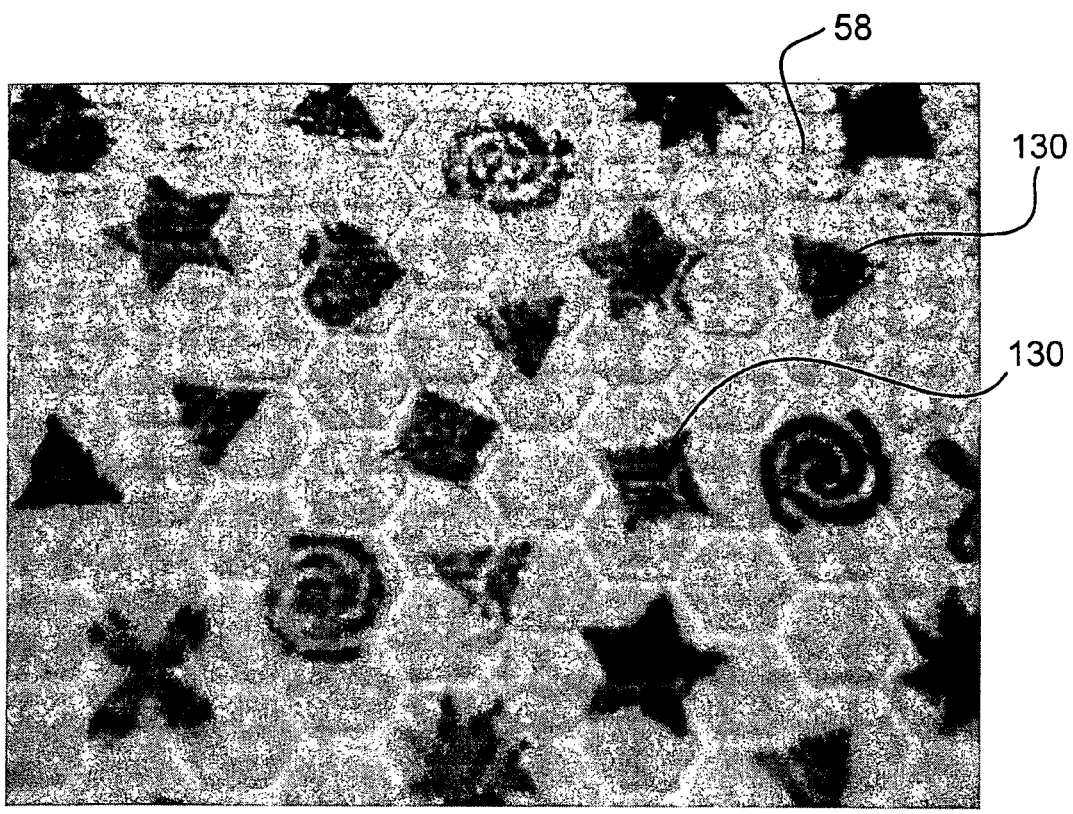
FIG. 7 is a photo of a loop material having an embossed pattern on its loop-carrying surface.
Figure 7A:
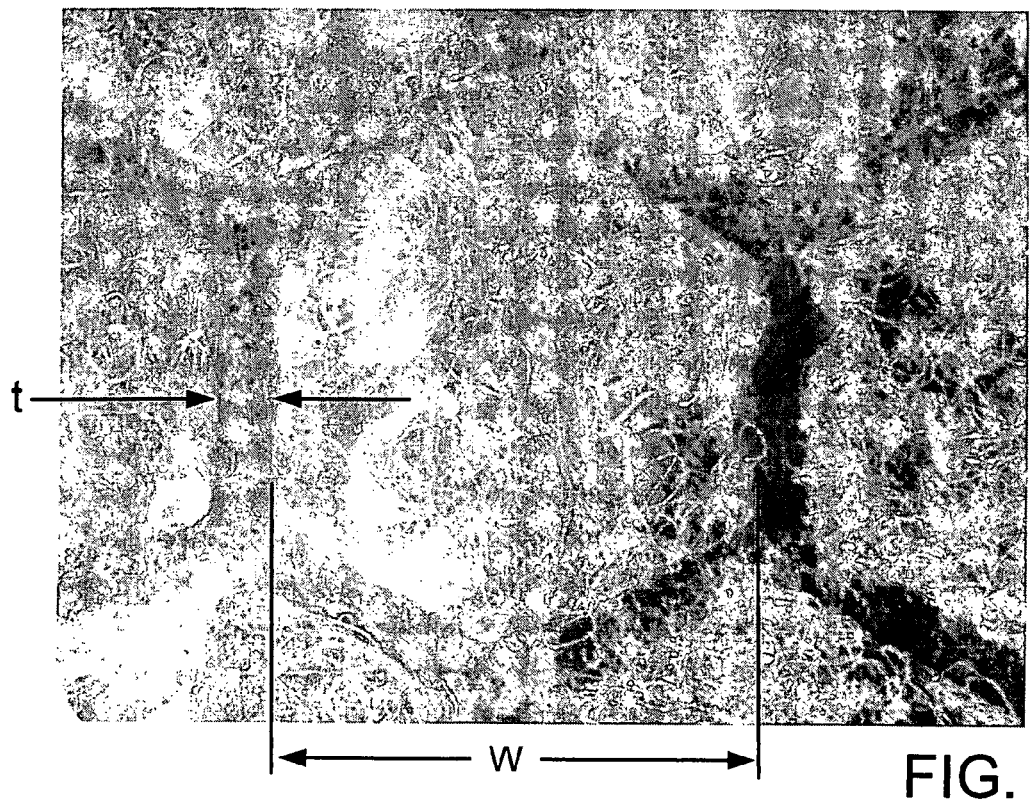
FIG. 7A is an enlarged view of one of the embossing cells, containing multiple discrete loop structures.

FIG. 7 shows a finished loop product, as seen from the loop side, embossed with a honeycomb pattern 58. In this example, graphic images 130 printed on the back side of the carrier film (opposite the loop side) are clearly visible through the loops. Printing on the back side of the film causes the ink to be encapsulated by fibers remaining on the back side of the film, to avoid ink wear. Various other embossing patterns include, as examples, a grid of intersecting lines forming squares or diamonds, or a pattern that crushes the loop formations other than in discrete regions of a desired shape, such as round pads of loops. The embossing pattern may also crush the loops to form a desired image, or text, on the loop material. As shown in FIG. 7A, each cell of the embossing pattern is a closed hexagon and contains multiple discrete loop structures. The width 'W' between opposite sides of the open area of the cell is about 6.5 millimeters, while the thickness 't' of the wall of the cell is about 0.8 millimeter.

Figure 8:
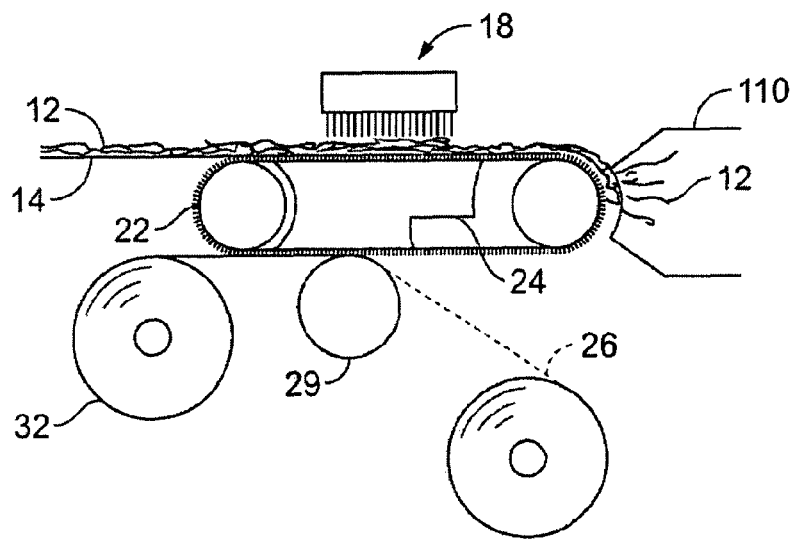
FIG. 8 is a diagrammatic view of a process for forming a loop material having discrete regions of loop while removing non-needled fibers from the carrier web.

Referring to FIG. 8, in one method of forming a product with only discrete regions of loop the fiber-covered carrier web is needled only in desired regions, leaving other areas of the web unpenetrated. The fibers in the non-needled regions remain generally loose and are readily removed from the carrier web, such as by vacuum 110. Removed fibers are readily re-carded and thus recycled. The needled web is then optionally laminated to a backing 26, fusing to the carrier sheet in the fiber-covered and needled regions as well as in the fiber-free regions. Alternatively, the fibers are fused to each other and/or the carrier sheet under pressure applied by hot can 29, without an added backing layer. The laminate product is then spooled, e.g., onto a take-up roll 32, for later use.

Figure 9:
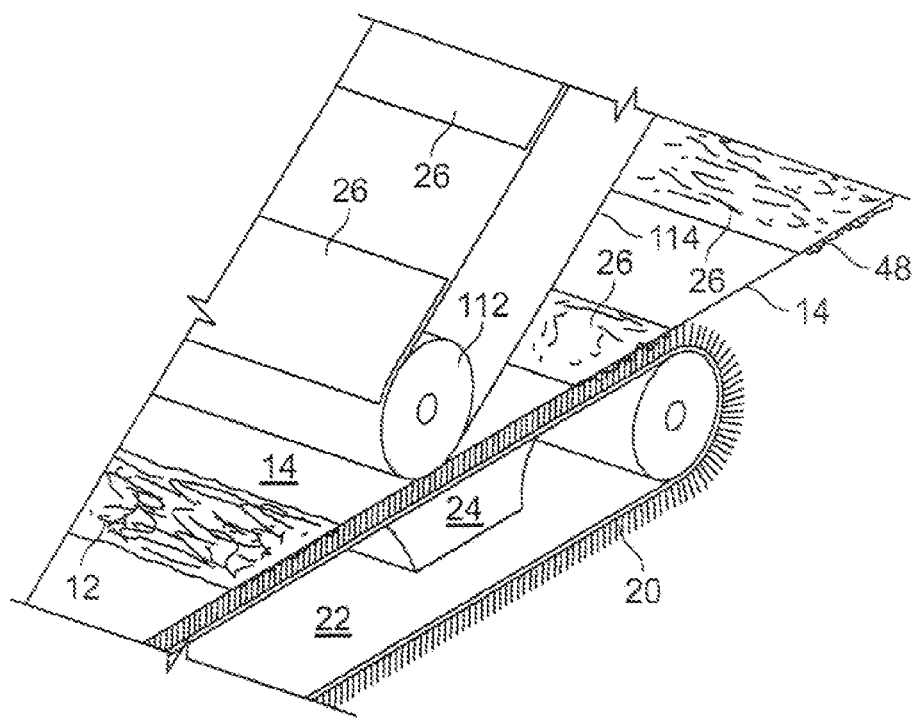
FIG. 9 is a diagrammatic view of a process for rendering needled portions of a loop product substantially fluid-impermeable.

In the alternative bonding process illustrated in FIG. 9, discrete patches of backing 26 are applied to cover the needled and fiber-bearing regions of carrier web 14, leaving the remaining regions of the carrier web uncovered and unlaminated. Each backing patch 26 is bonded in place by pressure from roller 112 to cover the fibers remaining on the back surface of the carrier web. Fluid impermeable patches 26 can be employed to seal the needled holes, thereby creating a fluid-impermeable finished product of particularly low weight and nominal thickness. In some cases, backing patches 26 are pre-coated with an adhesive that adheres the backing to the film and bonds the fibers. Patches 26 can be delivered to carrier 14 on a circulating conveyor belt 114 in a labeling process, as shown.

If the needled regions of the loop product are covered with a backing material 26 selected to be liquid impermeable, then the entire loop product can be formed to provide a barrier to liquids. If fibers 12 are selected to be absorbent, such as of cotton or cellulosic acetate, then the final loop product can be employed to wick liquids into the mat via the exposed loops 40.

Referring back to FIG. 1, another method of forming a product with only discrete regions of loop involves depositing staple fibers onto the carrier sheet 14 only in desired regions, leaving other regions of the carrier generally void of fibers, and then needling, laminating and embossing the sheet as described above, without regard to where the fibers are disposed. In this manner, loose fibers need not be removed from the product after needling. Discrete doses of fiber can be deposited onto the carrier through a template or screen, for example. Alternatively, the second carding doffer can be configured to supply discrete amounts of fibers to the condenser, or a light adhesive may be pre-applied to the carrier sheet only where fibers are desired, and then fibers applied over the extent of the film and removed where not lightly bonded.

Figure 10:
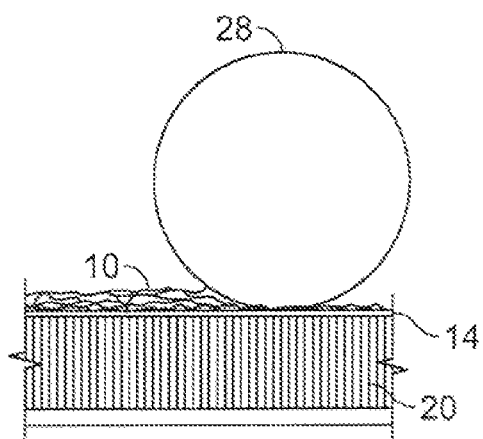
FIG. 10 is a diagrammatic view of an alternative process for forming a loop material having discrete regions of loop.
Figure 11:
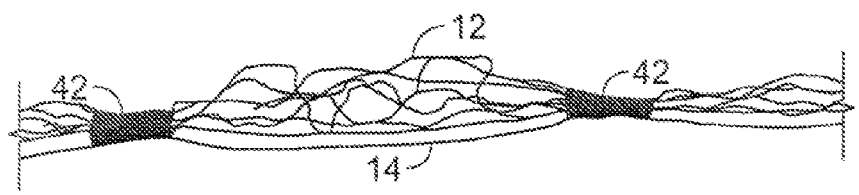
FIG. 11 is a highly enlarged diagrammatic view showing fibers bonded to each other and to a carrier at discrete bond points.

Another method of forming a loop product, illustrated in FIG. 10, employs no needling. Rather, the carded, crosslapped layer 10 of fibers is bonded to the carrier film 14 by lamination in a nip between a hot can 28 and a card clothcovered apron. By controlling the nip temperature, pressure and line speed, and by preheating the materials as needed, the fibers can be bonded directly to each other and to the carrier at discrete bond points 42 (FIG. 11), while leaving other fiber portions exposed for hook engagement. Additional loft may be maintained by orienting the bonding station such that the hot can 28 is on the underside of the carrier sheet 14, and the card cloth is wrapped about a counter-rotating roll engaging the fiber side of the product, such that fibers in regions between pins remains uncrushed. Product formed by this method differs from that formed by needling at least in that the working side of this product is the side of the carrier web onto which the fibers are originally placed. Additionally, the carrier sheet remains exposed for direct bonding to an underlying substrate, such as a compatible film.

A loop product with discrete loop regions may be formed by the method disclosed in FIG. 10 by selectively placing fibers only in regions where loops are required, and/or by configuring a card cloth-covered lamination roll to only have pins in regions where fiber bonding is desired.

Figure 12:
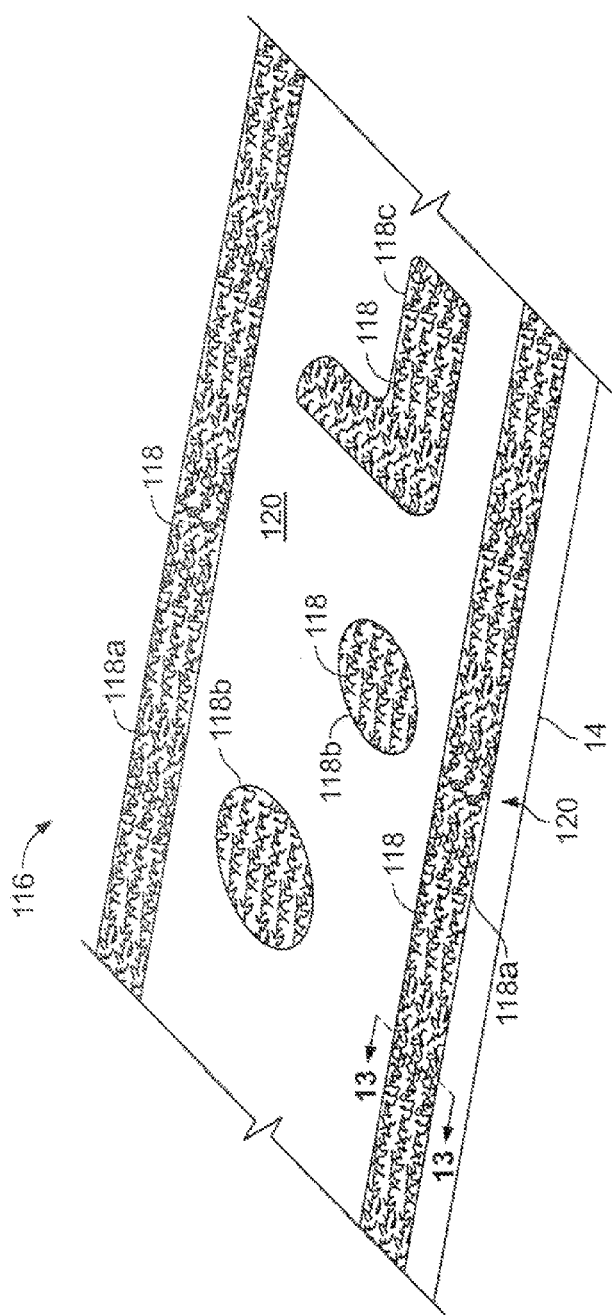
FIG. 12 is an enlarged perspective view of a loop material having fastening regions and loop-free regions.

A representative loop material 116 having discrete loop regions 118 and non-loop regions 120 is shown in FIG. 12. Loop regions 118 are spaced apart, and include longitudinally continuous lanes 118a and islands of loop that include circular patches 118b and a shaped, polygonal patch 118c. Nonloop regions 120 generally include all area of the loop material not in a loop region, and may be configured as one contiguous area surrounding multiple loop islands. The material may be embossed as described above, if desired, over its entire extent or only in the loop regions.

Figure 13B:
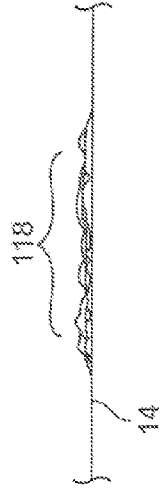
FIGS. 13A and 13B are cross-sectional views taken along line 13-13 in FIG. 12, showing alternate constructions.
Figure 13A:
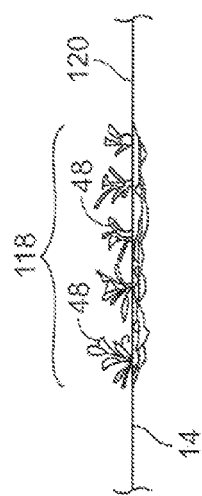

As shown in FIG. 13A, this particular example has been formed by needling staple fibers into a substrate 14, as described above with respect to FIG. 1. In the loop region shown, discrete loop structures 48 extend from the fastening side of the material, while a thin layer of base fibers extends across the loop region on an opposite side. These figures are not drawn to scale. In the alternative construction shown in FIG. 13B, the engageable loop fibers are exposed at a surface of a thin layer of bonded fibers on the fastening side, with the opposite side of the material remaining free of such fibers.

Figure 14:
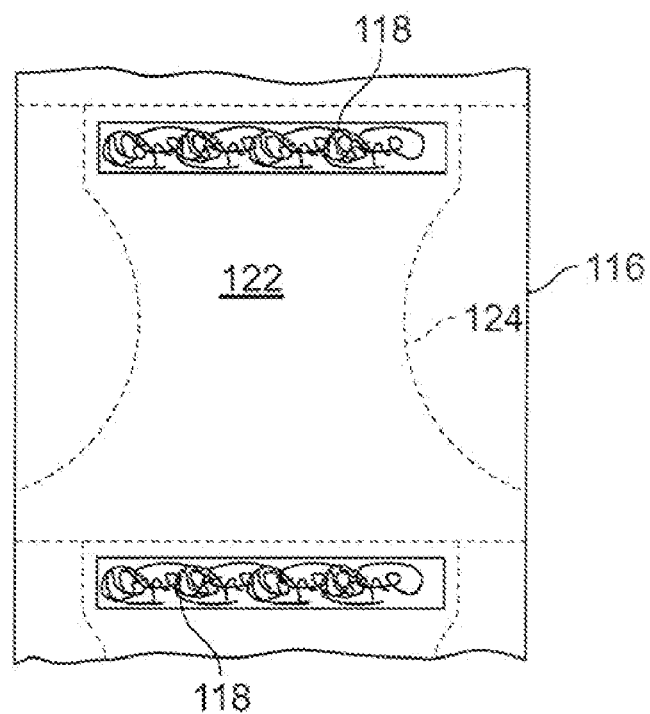
FIG. 14 is a top view of a sheet product with discrete loop regions, from which individual diaper covers may be die cut.

Thus, a material having loops only in desired regions may be manufactured. Such a product has utility, for example, as a continuous sheet product from which outer diaper covers may be die cut, as shown in FIG. 14. Each diaper body cover 122 is cut at dotted lines 124 to incorporate a discrete loop patch 118 of engageable fibers. Pre-printed graphics (not shown) on the substrate are indexed to the loop patch 118 and the die cutter and are visible through both the loop-bearing and loopfree regions of the carrier web.

Figure 15:
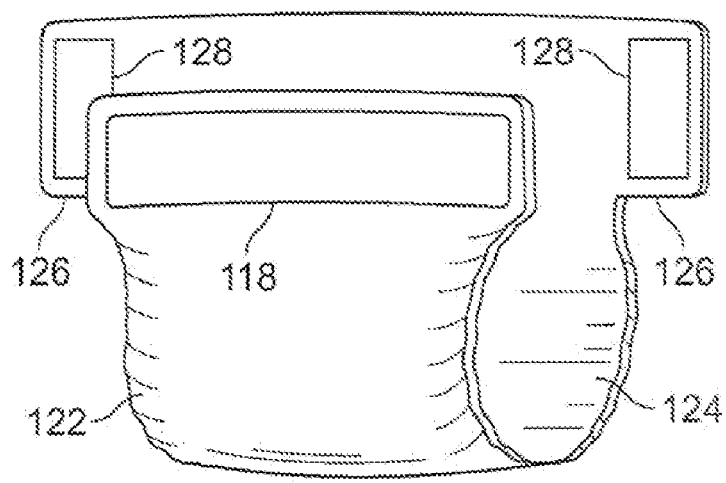
FIG. 15 is a perspective view of a disposable diaper having a diaper cover cut from the product of FIG. 14.

The die cut diaper cover 122 is formed into a disposable diaper as shown in FIG. 15, with the cover and an inner, porous film 124 sandwiching an absorbent core (not shown), and the loop patch 118 positioned to receive mating diaper tabs 126 carrying patches 128 of male fastener elements, to releasably secure the diaper about an infant. With loop structures formed directly through the material forming the outer cover of the diaper (according to the construction of FIG. 13A), there is no risk of the loop material delaminating or otherwise undesirably separating from the diaper chassis.

Figure 16:
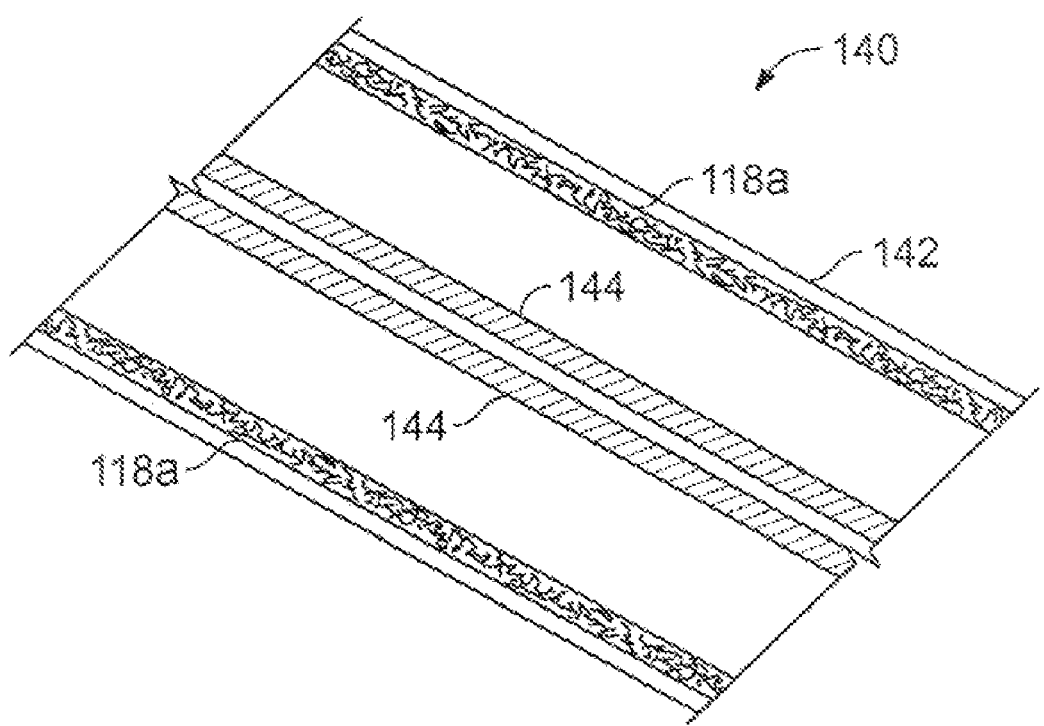
FIG. 16 is a perspective view of a sheet-form material with discrete loop regions and hook regions.

Referring to FIG. 16, in another application two discrete, spaced-apart, longitudinally continuous, parallel lanes of loop 118a are formed on a continuous sheet of film 142, such as polyethylene bag film, by the methods discussed above. The bag film with its loop lanes is then fed into a nip against a mold roll with two adjacent lanes of molten resin, which are bonded to the film in the nip while male fastener elements or stems for such elements are integrally molded from the resin, forming two continuous lanes 144 of male fastener elements or male fastener element preforms. The resulting product 140 shown in FIG. 16 can then be slit between lanes 144 to form two continuous sheets of material from which reclosable bags can be formed on standard bag-making equipment. If lanes 144 are molded with non-hook stems, the tops of such stems can be deformed prior to slitting to form engageable fastener elements. Loop lanes 118a need not be continuous, as the methods discussed above enable forming such lanes with gaps (not shown) at discrete intervals that can be indexed to the edge regions of bags where weld seals are to be formed, such that the loop fibers do not interfere with bag film welding. Methods of molding lanes of fastener elements are disclosed in U.S. patent application Ser. No. 09/808,395, published Feb. 21, 2002 as US2002/0022108 A1 now U.S. Pat. No. 7,048,818, and methods of making bags from continuous film with pre-applied fasteners are disclosed in pending U.S. application Ser. No. 10/357,608, published Dec. 11, 2003 as US2003/0228078 A1 now U.S. Pat. No. 6,991,375. Methods of making discrete patches of fastener elements on a carrier sheet are disclosed in pending U.S. application Ser. No. 10/803,682, now U.S. Pat. No. 7,438,847. The entire contents of all of these pending U.S. applications are hereby incorporated by reference, as if fully set forth.

Similarly, many other configurations of lanes or patches of hook and loop fasteners can be formed, where desired, on various substrate materials to form continuous material from which various useful products can be produced. The above methods also enable the production of material with discrete regions of loops that are not employed for fastening, but may be, for example, decorative or textural.

The above-described processes enable the cost-effective production of high volumes of materials with discrete regions of loops that may be configured to have good fastening characteristics. They can also be employed to produce loop materials in which the materials of the loops, substrate and optional backing are individually selected for optimal qualities. For example, the loop fiber material can be selected to have high tenacity for fastening strength, while the substrate and/or backing material can be selected to be readily bonded to other materials without harming the loop fibers. The materials of the loop product can also be selected for other desired properties.

In one case the loop fibers, carrier web and backing are all formed of polypropylene, making the finished loop product readily recyclable. In another example, the loop fibers, carrier web and backing are all of a biodegradable material, such that the finished loop product is more environmentally friendly. High tenacity fibers of biodegradable polylactic acid are available, for example, from Cargill Dow LLC under the trade name NATUREWORKS. In another example, carbon fibers are needle-punched into a KEVLAR film and bonded with silicone or other high temperature adhesive to produce a loop material with excellent fire resistance.

Polymer backing layers or binders may be selected from among suitable polyethylenes, polyesters, EVA, polypropylenes, and their co-polymers. Paper, fabric or even metal may be used. The binder may be applied in liquid or powder form, and may even be pre-coated on the fiber side of the carrier web before the fibers are applied. In many cases, a separate binder or backing layer is not required, such as for low cycle applications in disposable personal care products, such as diapers.

In one test, 3 denier crimped polyester fibers were carded and laid over an 0.002 inch (0.05 millimeter) thick sheet of blown polyethylene film in a layer having a basis weight of about 1.0 ounce per square yard (33 grams per square meter). The fiber-covered film was then needled with 38 gauge tufting needles, from the fiber side, at a needling density of 250 punches per square centimeter, and a penetration depth of 3.3 millimeters. The back of the needled material was bonded to a 0.001 inch (0.025 millimeter) thick sheet of polyethylene against a bed of pins. Mated with a molded hook product with CFM-29 hooks in a density of about 264 hooks per square centimeter from Velcro USA in Manchester, N.H., the loops achieved an average peel of about 500 grams per inch (200 grams per centimeter), as tested according to ASTM D 5170-91. Mated with this same hook product, the loop material achieved an average shear of about 7,000 grams per square inch (1100 grams per square centimeter), as tested according to ASTM D 5169-91. Tested against a CFM-85 palm tree hook from Velcro USA, the loop material achieved roughly 600 grams per inch (240 grams per centimeter) of peel and 6,000 grams per square inch (930 grams per square centimeter) of shear.

In another example, a loop product was prepared as in the test just described, except that the fibers were 6 denier, the needling density was 225 punches per square centimeter, and the needling depth was 4.4 centimeters. This loop material achieved roughly 550 grams per inch (215 grams per centimeter) of peel and 5,000 grams per square inch (775 grams per square centimeter) of shear against the CFM-29 hook product, and roughly 270 grams per inch (105 grams per centimeter) of peel and 5,500 grams per square inch (850 grams per square centimeter) of shear against the CFM-85 hook product.

In another test, the blend of 80 percent 3 denier crimped polyester fibers and 20 percent 4 denier bicomponent polyester fibers described above were carded and laid over an 0.0005 inch (0.013 millimeter) thick sheet of cast polypropylene film in a layer having a basis weight of about 1.0 ounce per square yard (34 grams per square meter). The fiber-covered film was then needled with 38 gauge fork needles, from the fiber side, at a needling density of 80 punches per square centimeter, and a penetration depth of 5.0 millimeters. The needled material was laminated with the lamination method described above with reference to FIG. 1. Mated with a molded hook product with CFM-69 hooks from Velcro USA, with a hook density of about 1,300 per square inch (200 hooks per square centimeter), the loops achieved an average peel of about 380 grams per inch (150 grams per centimeter), as tested according to ASTM D 5170-91. Mated with this same hook product, the loop material achieved an average shear of about 3,800 grams per square inch (600 grams per square centimeter), as tested according to ASTM D 5169-91. Mated with a molded hook product with CFM-108 hooks from Velcro USA (under part designation HTH 847), with a hook density of about 1,300 per square inch (200 hooks per square centimeter), the loops achieved an average peel of about 300 grams per inch (120 grams per centimeter), as tested according to ASTM D 5170-91. Mated with this same hook product, the loop material achieved an average shear of about 3,000 grams per square inch (475 grams per square centimeter), as tested according to ASTM D 5169-91.

A number of embodiments of the invention have been described. Nevertheless, it will be understood that various modifications may be made without departing from the spirit and scope of the invention. Accordingly, other embodiments are within the scope of the following claims.

What is claimed is:

1. A loop material for touch fastening, the loop material comprising:
   a flexible sheet-form substrate; and
   hook-engageable staple fibers needled through the substrate only in discrete fastening regions of the substrate, to form loops extending from a front side of the substrate in the discrete fastening regions,
   areas of the front side and an opposite back side of the substrate being free of staple fibers between adjacent discrete fastening regions;
   the staple fibers being secured to the back side of the substrate to anchor the loops.

2. The loop material of claim 1 wherein the fibers extend through holes pierced through the substrate.

3. The loop material of claim 1 wherein the fibers are fused to a surface of the substrate at discrete bonding locations within the fastening regions.

4. The loop material of claim 1 wherein the discrete fastening regions are surrounded by the areas of substrate that are free of staple fibers.

5. The loop material of claim 1 wherein the discrete fastening regions are circular.

6. The loop material of claim 1 wherein the discrete fastening regions comprise parallel lanes separated by the areas of substrate that are free of staple fibers.

7. The loop material of claim 6 wherein the lanes are longitudinally continuous.

8. The loop material of claim 1 wherein the substrate comprises a polymer film.

9. The loop material of claim 1 wherein the substrate comprises a scrim.

10. The loop material of claim 1 wherein the substrate comprises paper.

11. The loop material of claim 1 wherein the substrate defines parting lines defining individual fastening products therebetween, each fastening product containing an undivided one of the discrete fastening regions.

12. The loop material of claim 1 further comprising discrete, spaced apart regions of fastener elements.

13. The loop material of claim 1 wherein the fibers have strength, defined as tenacity times denier, of at least 8 grams.

14. The loop material of claim 1 wherein the fibers include bicomponent fibers having a core of one material and a sheath of another material, material of the sheaths of the bicomponent fibers binding fibers together.

15. The loop material of claim 1 having an overall weight of less than about 2 ounces per square yard (67 grams per square meter).

16. The loop material of claim 1 in a continuous length, spooled into roll form.

17. The loop material of claim 1 wherein the staple fibers were disposed on the substrate, prior to needling, in a layer of a total fiber weight of less than about 2 ounces per square yard (67 grams per square meter).

18. The loop material of claim 1 wherein the loop material has an overall weight of less than about 5 ounces per square yard (167 grams per square meter).

19. A loop material for touch fastening, the loop material comprising:
a flexible sheet-form substrate; and
hook-engageable staple fibers needled through the substrate and secured to a back side of the substrate,
wherein the fibers are secured to the back side of the substrate only in discrete fastening regions of the substrate, leaving areas of the back side and an opposite front side of the substrate free of staple fibers between adjacent discrete fastening regions.

20. The loop material of claim 19 wherein the discrete fastening regions are surrounded by the areas of substrate that are free of staple fibers.

21. The loop material of claim 20 wherein the discrete fastening regions are circular.

22. The loop material of claim 19 wherein the discrete fastening regions comprise parallel lanes separated by the areas of substrate that are free of staple fibers.

23. The loop material of claim 22 wherein the lanes are longitudinally continuous.

24. The loop material of claim 19 wherein the substrate defines parting lines defining individual fastening products therebetween, each fastening product containing an undivided one of the discrete fastening regions.

25. The loop material of claim 19 further comprising discrete, spaced apart regions of male fastener elements.

26. The loop material of claim 19 wherein the loop material has an overall weight of less than about 5 ounces per square yard (167 grams per square meter).

27. A loop material for touch fastening, the loop material comprising:
a flexible sheet-form substrate;
discrete, spaced apart regions of male fastener elements extending from a first surface of the substrate; and
staple fibers needled through the substrate from a back surface of the substrate to form hook-engageable loops extending from the first surface of the substrate and secured to the back surface of the substrate,
wherein the fibers are secured to the substrate only in discrete loop bearing regions of the substrate, leaving areas of the first and back surfaces of the substrate free of staple fibers between adjacent discrete loop bearing regions.

* * * * *